(12) United States Patent
Bagci et al.

(10) Patent No.: US 11,730,387 B2
(45) Date of Patent: Aug. 22, 2023

(54) METHOD FOR DETECTION AND DIAGNOSIS OF LUNG AND PANCREATIC CANCERS FROM IMAGING SCANS

(71) Applicant: University of Central Florida Research Foundation, Inc., Orlando, FL (US)

(72) Inventors: Ulas Bagci, Orlando, FL (US); Naji Khosravan, Orlando, FL (US); Sarfaraz Hussein, Orlando, FL (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 649 days.

(21) Appl. No.: 16/673,397

(22) Filed: Nov. 4, 2019

(65) Prior Publication Data

US 2020/0160997 A1    May 21, 2020

Related U.S. Application Data

(60) Provisional application No. 62/755,018, filed on Nov. 2, 2018.

(51) Int. Cl.
*A61B 5/00* (2006.01)
*A61B 5/055* (2006.01)
(Continued)

(52) U.S. Cl.
CPC ............ *A61B 5/055* (2013.01); *A61B 6/032* (2013.01); *A61B 6/037* (2013.01); *A61B 6/4417* (2013.01);
(Continued)

(58) Field of Classification Search
None
See application file for complete search history.

(56) References Cited

U.S. PATENT DOCUMENTS

| | | | |
|---|---|---|---|
| 9,934,364 B1* | 4/2018 | Kumar | G16B 25/10 |
| 2013/0040803 A1* | 2/2013 | Seal | B01J 20/3238 |
| | | | 502/401 |

(Continued)

OTHER PUBLICATIONS

Al-masni et al., "Simultaneous detection and classification of breast masses in digital mammograms via a deep learning YOLO-based CAD system," Computer Methods and Programs in Biomedicine 157 (2018) 85-94 (Year: 2018).*

(Continued)

*Primary Examiner* — Soo Shin
(74) *Attorney, Agent, or Firm* — Michele L. Lawson; Smith & Hopen, P.A.

(57) ABSTRACT

A method of detecting and diagnosing cancers characterized by the presence of at least one nodule/neoplasm from an imaging scan is presented. To detect nodules in an imaging scan, a 3D CNN using a single feed forward pass of a single network is used. After detection, risk stratification is performed using a supervised or an unsupervised deep learning method to assist in characterizing the detected nodule/neoplasm as benign or malignant. The supervised learning method relies on a 3D CNN used with transfer learning and a graph regularized sparse MTL to determine malignancy. The unsupervised learning method uses clustering to generate labels after which label proportions are used with a novel algorithm to classify malignancy. The method assists radiologists in improving detection rates of lung nodules to facilitate early detection and minimizing errors in diagnosis.

20 Claims, 9 Drawing Sheets
(8 of 9 Drawing Sheet(s) Filed in Color)

(51) Int. Cl.
| | |
|---|---|
| A61B 6/00 | (2006.01) |
| A61B 6/03 | (2006.01) |
| A61B 6/12 | (2006.01) |
| A61B 8/08 | (2006.01) |
| G16H 50/20 | (2018.01) |
| G06N 3/04 | (2023.01) |
| G06N 20/10 | (2019.01) |
| G06N 5/04 | (2023.01) |
| G06N 3/08 | (2023.01) |
| G16H 30/40 | (2018.01) |
| G16H 70/60 | (2018.01) |
| G06T 7/00 | (2017.01) |
| G06F 18/23 | (2023.01) |
| G06F 18/214 | (2023.01) |
| G06F 18/2411 | (2023.01) |
| G06V 10/764 | (2022.01) |
| G06V 10/82 | (2022.01) |

(52) U.S. Cl.
CPC ............ *A61B 6/5217* (2013.01); *A61B 8/481* (2013.01); *A61B 8/5223* (2013.01); *G06F 18/2148* (2023.01); *G06F 18/23* (2023.01); *G06F 18/2411* (2023.01); *G06N 3/04* (2013.01); *G06N 3/08* (2013.01); *G06N 5/04* (2013.01); *G06N 20/10* (2019.01); *G06T 7/0012* (2013.01); *G06V 10/764* (2022.01); *G06V 10/82* (2022.01); *G16H 30/40* (2018.01); *G16H 50/20* (2018.01); *G16H 70/60* (2018.01); *G06T 2207/10081* (2013.01); *G06T 2207/20076* (2013.01); *G06T 2207/20081* (2013.01); *G06T 2207/20084* (2013.01); *G06T 2207/30064* (2013.01); *G06T 2207/30096* (2013.01); *G06V 2201/032* (2022.01)

(56) References Cited

U.S. PATENT DOCUMENTS

| | | | | |
|---|---|---|---|---|
| 2017/0360412 | A1* | 12/2017 | Rothberg | G06T 11/60 |
| 2018/0247195 | A1* | 8/2018 | Kumar | G06N 3/08 |
| 2020/0005899 | A1* | 1/2020 | Nicula | G16H 50/20 |
| 2020/0363414 | A1* | 11/2020 | Yelensky | C12N 5/0636 |

OTHER PUBLICATIONS

Fan et al., "Dual-Graph Regularized Discriminative Multitask Tracker," IEEE Transactions on Multimedia, vol. 20, No. 9, Sep. 2018 (Year: 2018).*
Freedman, "Computer Assisted Quality Control and Telemammography," Grant No. DAMD17-93-J-3015, Georgetown University, Aug. 1996 (Year: 1996).*
Yu et al., "∝SVM for Learning with Label Proportions," arXiv:1306.0886v1 [cs.LG] Jun. 4, 2013 (Year: 2013).*
Lopez, et al. Large scale validation of the m5l lung CAD on heterogeneous CT datasets. Medical Physics 42(4), 1477-1489 (Apr. 2015).
Sivakumar and Chandrasekar. Lung Nodule Segmentation through Unsupervised Clustering Models. Procedia Engineering 38 (2012) 3064 3073.
Chatfield, et al. Return of the Devil in the Details: Delving Deep into Convolutional Nets. In: British Machine Vision Conference. arXiv:1405.3531(2014). Visual Geometry Group, Department of Engineering at University of Oxford.
Radford and Metz. Unsupervised Representation Learning with Deep Convolutional Generative Adversarial Networks. arXiv:1511.06434 (2015).
Buty, et al. Characterization of Lung Nodule Malignancy Using Hybrid Shape and Appearance Features. In: MICCAI. arXiv:1609.06668 (2016).
Ypsilantis and Montana. Recurrent Convolutional Networks for Pulmonary Nodule Detection in CT Imaging. arXiv:1609.09143 (2016). Department of Biomedical Engineering at King's College London.
Hussein, et al. Lung Nodule Characterization Using Multi-View Convolutional Neural Network with Gaussian Process. arXiv:1703.00645 (2017). Center for Research in Computer Vision (CRCV) at the University of Central Florida.
Hussein, et al. Risk Stratification of Lung Nodules Using 3D CNN-Based Multi-Task Learning. arXiv:1704.08797 (2017). Center for Research in Computer Vision (CRCV) at the University of Central Florida.
Ding, et al. Accurate Pulmonary Nodule Detection in Computed Tomography Images Using Deep Convolutional Neural Networks. arXiv:1706.04303 (2017). School of EECS at Peking University.
Furuya, et al. New Classification of Small Pulmonary Nodules by Margin Characteristics on Highresolution CT. Acta Radiologica 40(5), 496-504 (1999).
Zhou, et al. Deep Supervision for Pancreatic Cyst Segmentation in Abdominal CT Scans. arXiv:1706.07346 (2017). The Johns Hopkins University School of Medicine.
Khosravan and Bagci. S4ND: Single-Shot Single-Scale Lung Nodule Detection. arXiv:1805.02279 (2018). Center for Research in Computer Vision (CRCV), School of Computer Science, University of Central Florida.
Kumar, et al. Lung Nodule Classification Using Deep Features in CT Images. In: Computer and Robot Vision (CRV), 2015 12th Conference on. pp. 133-138. IEEE (2015).
Dou, et al. Multilevel contextual 3-D CNNs for False Positive Reduction in Pulmonary Nodule Detection. IEEE Transactions on Biomedical Engineering 64(7), 1558-1567 (2017).
Liu, et al. SSD: Single Shot Multibox Detector. arXiv:1512.02325 (2016). In: European conference on computer vision.
Lee, et al. Unsupervised Feature Learning for Audio Classification Using Convolutional Deep Belief Networks. In Advances in neural information processing systems. pp. 1096-1104 (2009).
Zhang, et al. A Ranking-Based Lung Nodule Image Classification Method Using Unlabeled Image Knowledge. In: IEEE ISBI. pp. 1356-1359. IEEE (2014).
Setio, et al. Validation, comparison, and combination of algorithms for automatic detection of pulmonary nodules in computed tomography images: The LUNA16 challenge. arXiv:1612.08012 (Aug. 2017). Medical Image Analysis 42 (Supplement C), 1-13.
Naceur, et al. Fully Automatic Brain Tumor Segmentation using End-to-End Incremental Deep Neural Networks in MRI images. Computer Methods and Programs in Biomedicine Elsevier, 2018. 166, pp. 39-49.
Kamper, et al. Fully Unsupervised Small-Vocabulary Speech Recognition Using a Segmental Bayesian Model. In: Interspeech (2015).
Gazit, et al. Quantification of CT Images for the Classification of High and Low Risk Pancreatic Cysts. In: SPIE Medical Imaging. pp. 101340X-101340X. International Society for Optics and Photonics (2017).
Ardila, et al. End-to-End Lung Cancer Screening with Three-Dimensional Deep Learning on Low-Dose Chest Computed Tomography. Nature Medicine, vol. 25, Jun. 2019; pp. 954-961.
Way, et al. Computer-aided diagnosis of pulmonary nodules on CT scans: Segmentation and classification using 3D active contours. Medical Physics 33(7), 2323-2337 (2006).
Cai, et al. Pancreas Segmentation in MRI using Graph-Based Decision Fusion on Convolutional Neural Networks. Med Image Comput Comput Assist Iterv. Oct. 2016; 9901: pp. 442-450.
Hanania, et al. Quantitative imaging to evaluate malignant potential of IPMNs. Oncotarget, 2016, vol. 7, No. 52, pp. 85776-85784.
Uchiyama, et al. Quantitative computerized analysis of diffuse lung disease in high-resolution computed tomography. Medical Physics 30(9), 2440-2454 (2003).
Setio, et al. Pulmonary Nodule Detection in CT Images: False Positive Reduction Using Multi-View Convolutional Networks. IEEE transactions on Medical Imaging, 35(5), 1160-1169 (2016).

(56) References Cited

OTHER PUBLICATIONS

Shalev-Shwartz and Tewari. Stochastic methods for l1-regularized Loss Minimization. Journal of Machine Learning Research 12 (2011), 1865-1892.
Ciompi et al. Towards automatic pulmonary nodule management in lung cancer screening with deep learning. Scientific reports 7:46479 (2017).
Shin, et al. Stacked Autoencoders for Unsupervised Feature Learning and Multiple Organ Detection in a Pilot Study Using 4D Patient Data. IEEE Transactions on Pattern Analysis and Machine Intelligence 35(8), 1930-1943 (2013).
Huang, et al. Lung Nodule Detection in CT Using 3D Convolutional Neural Networks. In: Biomedical Imaging (ISBI 2017), 2017 IEEE 14th International Symposium on. pp. 379-383. IEEE (2017).
Kallenberg, et al. Unsupervised deep learning applied to breast density segmentation and mammographic risk scoring. IEEE transactions on medical imaging 35(5), 1322-1331 (2016).
Hussein, et al. Supervised and Unsupervised Tumor Characterization in the Deep Learning Era. arXiv:1801.03230 (2018). IEEE Transactions on Medical Imaging.
Anonymous. Lung Nodule Classification using Label Proportions: An Unsupervised Approach. Paper ID: 734. NICCAI 2017 Submission.
El-Baz, et al. 3D Shape Analysis for Early Diagnosis of Malignant Lung Nodules. MICCAI 2011, Part III, LNCS 6893, pp. 175-182.
Han, et al. Texture Feature Analysis for Computer-Aided Diagnosis on Pulmonary Nodules. Journal of Digital Imaging 28(1), 99-115 (2015).
Krishnamurthy, et al. An automatic Computerized Model for Cancerous Lung Nodule Detection from Computed Tomography Images with Reduced False Positives. In: International Conference on Recent Trends in Image Processing and Pattern Recognition, 2017: pp. 343-355.
Sivic, et al. Discovering objects and their location in images. In: ICCV. vol. 1, pp. 370-377. IEEE (2005).
Lee, et al. Computer-aided diagnosis of pulmonary nodules using a two-step approach for feature selection and classifier ensemble construction. Artificial Intelligence in Medicine 50(2010), 43-53.
Golan, et al. Lung Nodule Detection in CT Images Using Deep Convolutional Neural Networks. In: Neural Networks (IJCNN), 2016 International Joint Conference on. pp. 243-250. IEEE (2016).
Shen, et al. Multi-scale convolutional neural networks for lung nodule classification. In: IPMI. pp. 588-599.Springer (2015).
Vincent, et al. Stacked Denoising Autoencoders: Learning Useful Representations in a Deep Network with a Local Denoising Criterion. Journal of Machine Learning Research 11 (2010) 3371-3408.
Hussein, et al. Lung and Pancreatic Tumor Characterization in the Deep Learning Era: Novel Supervised and Unsupervised Learning Approaches. arXiv:1801.03230 (2019).
Huang, Gao et al. Densley Connected Convolutional Networks. Proceedings of the IEEE Conference on Computer Vision and Pattern Recognition (CVPR), 2017, pp. 4700-4708.

\* cited by examiner

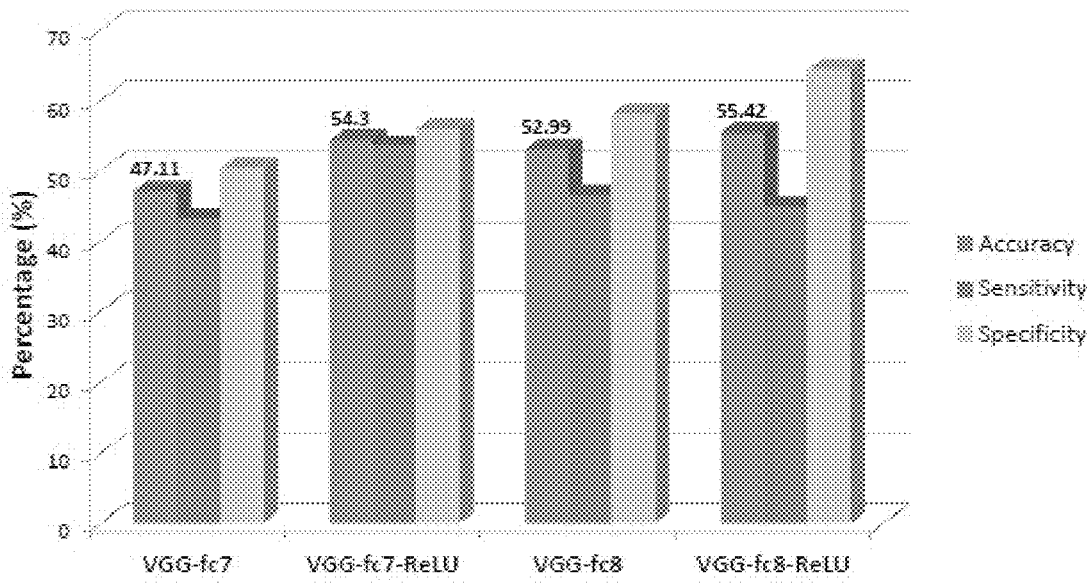
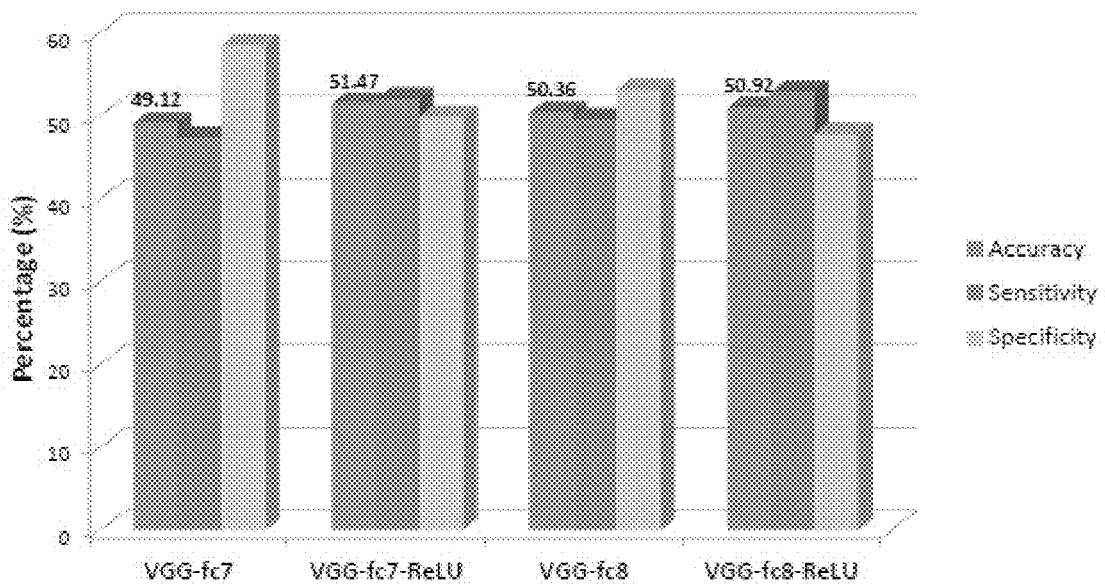
Figure 8A-B

METHOD FOR DETECTION AND DIAGNOSIS OF LUNG AND PANCREATIC CANCERS FROM IMAGING SCANS

CROSS REFERENCE TO RELATED APPLICATIONS

This application claims priority to U.S. Provisional Application No. 62/755,018 entitled "Fast and Reliable Detection and Diagnosis of Lung Cancers from CT Scans", filed Nov. 2, 2018, the contents of which are hereby incorporated by reference into this disclosure.

FIELD OF INVENTION

This invention relates to methods of detecting and diagnosing cancer. Specifically, the invention describes a method of screening and diagnosis of lung cancer from CT scans.

BACKGROUND OF THE INVENTION

According to the American Cancer Society, approximately 40% of people will be diagnosed with cancer at some point during their lifetime with an overall mortality of 171.2 per 100,000 people per year (based on deaths between 2008-2012). Lung and pancreatic cancers are two of the most common cancers. While lung cancer is the largest cause of cancer-related deaths in the world, pancreatic cancer has the poorest prognosis with a 5-year survival rate of only 7% in the United States. With regards to pancreatic cancer, specifically in this work, the inventors focus on the challenging problem of automatic diagnosis of Intraductal Papillary Mucinous Neoplasms (IPMN). IPMN is a pre-malignant condition and if left untreated, it can progress to invasive cancer. IPMN is mucin-producing neoplasm that can be found in the main pancreatic duct and its branches. They are radiographically identifiable precursors to pancreatic cancer. Detection and characterization of these lung and pancreatic tumors can aid in early diagnosis; hence, increased survival chance through appropriate treatment/surgery plans.

Conventionally, the computer-aided detection (CAD) systems are designed to assist radiologists in making accurate and fast decisions by reducing the number of false positives and false negatives. For diagnostic decision making, a higher emphasis is laid on increased sensitivity: a false-flag is more tolerable than a tumor being missed or incorrectly classified as benign. In this regard, a computerized analysis of imaging features becomes a key instrument for radiologists to improve their diagnostic decisions. In the literature, automated detection and diagnosis methods had been developed for tumors in different organs such as breast, colon, brain, lung, liver, prostate, and others. As is typical in such studies, a CAD includes preprocessing and feature engineering steps (including feature extraction and selection) followed by a classification step. (El-Baz, A., Nitzken, M., Khalifa, F., Elnakib, A., Gimelfarb, G., Falk, R., El-Ghar, M. A.: 3D shape analysis for early diagnosis of malignant lung nodules. In: IPMI. pp. 772-783. Springer (2011); Han, F., Wang, H., Zhang, G., Han, H., Song, B., Li, L., Moore, W., Lu, H., Zhao, H., Liang, Z.: Texture feature analysis for computer-aided diagnosis on pulmonary nodules. Journal of Digital Imaging 28(1), 99-115 (2015); Way, T. W., Hadjiiski, L. M., Sahiner, B., Chan, H. P., Cascade, P. N., Kazerooni, E.A., Bogot, N., Zhou, C.: Computer-aided diagnosis of pulmonary nodules on CT scans: segmentation and classification using 3D active contours. Medical Physics 33(7), 2323-2337 (2006); Lee, M., Boroczky, L., Sungur-Stasik, K., Cann, A., Borczuk, A., Kawut, S., Powell, C.: Computer-aided diagnosis of pulmonary nodules using a two-step approach for feature selection and classifier ensemble construction. Artificial Intelligence in Medicine 50(1), 43-53 (2010)).

However, with the success of deep learning, a transition from feature engineering to feature learning has been observed in medical image analysis literature. Those systems comprise Convolutional Neural Networks (CNN) as feature extractor followed by a conventional classifier such as Random Forest (RF). (Kumar, D., Wong, A., Clausi, D. A.: Lung nodule classification using deep features in CT images. In: Computer and Robot Vision (CRV), 2015 12th Conference on. pp. 133-138. IEEE (2015); Buty, M., Xu, Z., Gao, M., Bagci, U., Wu, A., Mollura, D. J.: Characterization of Lung Nodule Malignancy Using Hybrid Shape and Appearance Features. In: MICCAI. pp. 662-670. Springer (2016)). In scenarios where a large number of labeled training examples are available, however, end-to-end trainable deep learning approaches can be employed. (Saouli, R., Akil, M., Kachouri, R., et al.: Fully automatic brain tumor segmentation using end-to-end incremental deep neural networks in mri images. Computer methods and programs in biomedicine 166, 39-49 (2018)).

Detection of Lung Nodules

Successful diagnosis and treatment of lung cancer is highly dependent on early detection of lung nodules. Radiologists are analyzing an increasing amount of imaging data (CT scans) every day. Computer Aided Detection (CAD) systems are designed to help radiologists in the screening process. However, automatic detection of lung nodules with CADs remains a challenging task. One reason is the high variation in texture, shape, and position of nodules in CT scans, and their similarity with other nearby structures. Another reason is the discrepancy between the large search space (i.e., entire lung fields) and respectively tiny nature of the nodules. Detection of tiny/small objects has remained a very challenging task in computer vision, which so far has only been solved using computationally expensive multi-stage frameworks. Current state of art methods for lung nodule detection follow the same multi-stage detection frameworks as in other computer vision areas.

The literature for lung nodule detection and diagnosis is vast. To date, the common strategy for all available CAD systems for lung nodule detection is to use a candidate identification step (also known as region proposal). While some of these studies apply low-level appearance-based features as a prior to drive this identification task, others use shape and size information. (Lopez Tones, E., Fiorina, E., Pennazio, F., Peroni, C., Saletta, M., Camarlinghi, N., Fantacci, M., Cerello, P.: Large scale validation of the m51 lung cad on hetero-geneous ct datasets. Medical physics 42(4), 1477-1489 (2015); Krishnamurthy, S., Narasimhan, G., Rengasamy, U.: An automatic computerized model for cancerous lung nodule detection from computed tomography images with reduced false positives. In: International Conference on Recent Trends in Image Processing and Pattern Recognition. pp. 343-355. Springer (2016)). Related to deep learning-based methods, Ypsilantis et al. proposed to use recurrent neural networks in a patch-based strategy to improve nodule detection. (Ypsilantis, P. P., Montana, G.: Recurrent convolutional networks for pulmonary nodule detection in ct imaging. arXiv preprint arXiv:1609.09143 (2016)). Krishnamurthy et al. proposed to detect candidates using a 2D multi-step segmentation process. Then a group of hand-crafted features were extracted, followed by a two-stage classification of candidates. (Krishnamurthy, 2016).

In a similar fashion, Huang et al. proposed a geometric model-based candidate detection method which followed by a 3D CNN to reduce number of FPs. (Huang, X., Shan, J., Vaidya, V.: Lung nodule detection in ct using 3d convolutional neural networks. In: Biomedical Imaging (ISBI 2017), 2017 IEEE 14th International Symposium on. pp. 379-383. IEEE (2017)). Golan et al. used a deep 3D CNN with a small input patch of 5×20×20 for lung nodule detection. The network was applied to the lung CT volume multiple times using a sliding window and exhaustive search strategy to output a probability map over the volume. (Golan, R., Jacob, C., Denzinger, J.: Lung nodule detection in ct images using deep convolutional neural networks. In: Neural Networks (IJCNN), 2016 International Joint Conference on. pp. 243-250. IEEE (2016)).

There has, also, been detailed investigations of high-level discriminatory information extraction using deep networks to perform a better FP reduction.(Setio, A. A. A., Ciompi, F., Litjens, G., Gerke, P., Jacobs, C., van Riel, S. J., Wille, M. M. W., Naqibullah, M., S'anchez, C. I., van Ginneken, B.: Pulmonary nodule detection in ct images: false positive reduction using multi-view convolutional net-works. IEEE transactions on medical imaging 35(5), 1160-1169 (2016)). Setio et al. used 9 separate 2D convolutional neural networks trained on 9 different views of candidates, followed by a fusion strategy to perform FP reduction. (Setio, 2016). Another study used a modified version of Faster R-CNN, state of the art object detector at the time, for candidate detection and a patch-based 3D CNN for FP reduction step. (Ding, J., Li, A., Hu, Z., Wang, L.: Accurate pulmonary nodule detection in computed tomography images using deep convolutional neural networks. In: International Conference on Medical Image Computing and Computer-Assisted Intervention. pp. 559-567. Springer (2017)). However, all these methods are computationally inefficient (e.g., exhaustive use of sliding windows over feature maps), and often computed in 2D manner, not appreciating the 3D nature of the nodule space. It is worth mentioning that patch-based methods are 3D but they suffer from the same computational burdens, as well as missing the entire notion of 3D nodule space due to limited information available in the patches.

The inventors resolve the aforementioned issues by proposing a completely 3D deep network architecture designed to detect lung nodules in a single shot using a single-scale network. The inventors are the first to perform lung nodule detection in one step. Specific to the architecture design of the deep network, the inventors make use of convolution blocks with dense connections for this problem, making one step nodule detection computationally feasible. The inventors also investigate and justify the effect of different downsampling methods in the network due to its important role for tiny object detection. Lastly, the inventors argue that lung nodule detection, as opposed to object detection in natural images, can be done with high accuracy using only a single scale network when network is carefully designed with its hyper-parameters.

Classification of Lung Nodules

Imaging Features and Classifiers: Conventionally, the risk stratification (classification) of lung nodules may require nodule segmentation, computation and selection of low-level features from the image, and the use of a classifier/regressor. In the approach by Uchiyama, different physical statistics including intensity measures were extracted and class labels were obtained using Artificial Neural Networks. (Uchiyama, Y., Katsuragawa, S., Abe, H., Shiraishi, J., Li, F., Li, Q., Zhang, C.T., Suzuki, K., Doi, K.: Quantitative computerized analysis of diffuse lung disease in high-resolution computed tomography. Medical Physics 30(9), 2440-2454 (2003)). El-Baz segmented lung nodules using appearance-based models followed by shape analysis using spherical harmonics. (El-Baz, 2011). The last step involved k-nearest neighbor-based classification. Another approach extended 2D texture features including Local Binary Patterns, Gabor and Haralick to 3D. (Han, 2015). Classification using Support Vector Machine (SVM) was performed as the final step. In a different study, Way et al. implemented nodule segmentation via 3D active contours, and then applied rubber band straightening transform. A Linear Discriminant Analysis (LDA) classifier was applied to get class labels. (Way 2006). Lee et al. introduced a feature selection-based approach utilizing both clinical and imaging data. Information content and feature relevance were measured using an ensemble of genetic algorithm and random subspace method. (Lee, 2010). Lastly, LDA was applied to obtain final classification on the condensed feature set. In a recent work, spherical harmonics features were fused with deep learning features and then RF classification was employed for lung nodule characterization. (Buty, 2016). Up until now, the application of CNN for nodule characterization has been limited to 2D space, thus falling short of incorporating vital contextual and volumetric information. (Uchiyama, Y., Katsuragawa, S., Abe, H., Shiraishi, J., Li, F., Li, Q., Zhang, C.T., Suzuki, K., Doi, K.: Quantitative computerized analysis of diffuse lung disease in high-resolution computed tomography. Medical Physics 30(9), 2440-2454 (2003)). In another approach, Shin et al. employed CNN for the classification of lung nodules. (Shen, W., Zhou, M., Yang, F., Yang, C., Tian, J.: Multi-scale convolutional neural networks for lung nodule classification. In: IPMI. pp. 588-599. Springer (2015)). Other than not completely 3D CNN, the approach didn't take into account high-level nodule attributes and required training an off-the-shelf classifier such as RF and SVM.

The information about different high-level image attributes had been found useful in the malignancy characterization of lung nodules. In a study exploring the correlation between malignancy and nodule attributes, Furuya found that 82% of the lobulated, 93% of the ragged, 97% of the densely spiculated, and 100% of the halo nodules were malignant in a particular dataset. (Furuya, K., Murayama, S., Soeda, H., Murakami, J., Ichinose, Y., Yauuchi, H., Katsuda, Y., Koga, M., Masuda, K.: New classification of small pulmonary nodules by margin characteristics on high resolution CT. Acta Radiologica 40(5), 496-504 (1999)). Automatic determination of lung nodule attributes and types had been explored by Ciompi. (Ciompi, F., Chung, K., Van Riel, S. J., Setio, A. A. A., Gerke, P. K., Jacobs, C., Scholten, E. T., Schaefer-Prokop, C., Wille, M. M., Marchiano, A., et al.: Towards automatic pulmonary nodule management in lung cancer screening with deep learning. Scientific reports 7, 46479 (2017)). The objective was to perform the classification of six different nodule types such as solid, non-solid, part-solid, calcified, perifissural and spiculated nodules. However, the approach is based on 2D CNN and fell short of estimating the malignancy of lung nodules. Furthermore, 66% of the round nodules were determined as benign.

Classification of Pancreatic Cysts (IPMN)

Although there has been considerable progress in developing automatic approaches to segment pancreas and its cysts, the use of advanced machine learning algorithms to perform fully automatic risk-stratification of IPMNs is limited. (Zhou, Y., Xie, L., Fishman, E. K., Yuille, A. L.: Deep Supervision for Pancreatic Cyst Segmentation in Abdominal CT Scans. arXiv preprint arXiv:1706.07346 (2017); Cai, J., Lu, L., Zhang, Z., Xing, F., Yang, L., Yin, Q.: Pancreas segmentation in MiII using graph-based decision fusion on convolutional neural networks. In: MICCAI. pp. 442-450. Springer (2016)). The approach by Hanania et al. investigated the influence of 360 imaging features ranging from intensity, texture, and shape to stratify subjects as low or high-grade IPMN. In another example, Gazit et al. extracted texture and features from the solid component of segmented cysts followed by a feature selection and classification scheme. Both of these approaches required segmentation of cysts or pancreas and are evaluated on CT scans only. (Hanania, A. N., Bantis, L. E., Feng, Z., Wang, H., Tamm, E. P., Katz, M. H., Maitra, A., Koay, E. J.: Quantitative imaging to evaluate malignant potential of IPMNs. Oncotarget 7(52), 85776 (2016); Gazit, L., Chakraborty, J., Attiyeh, M., Langdon-Embry, L., Allen, P. J., Do, R. K., Simpson, A. L.: Quantification of CT Images for the Classification of High-and Low-Risk Pancreatic Cysts. In: SPIE Medical Imaging. pp. 101340X-101340X. International Society for Optics and Photonics (2017)).

In contrast, the inventors proposed approach does not require segmentation of cysts or pancreas but rather evaluates IPMNs on MRI scans which is a preferred modality because there is no radiation exposure and improved soft-tissue contrast. The study disclosed herein is the largest IPMN classification study consisting of 171 subjects across both modalities (CT and MRI).

Unsupervised Learning

Typically, the visual recognition and classification tasks are addressed using labeled data (supervision). However, for tasks where manually generating labels corresponding to large datasets is laborious and expensive, the use of unsupervised learning methods is of significant value. Unsupervised techniques had been used to solve problems in various domains ranging from object categorization, speech processing, and audio classification. (Sivic, J., Russell, B.C., Efros, A. A., Zisserman, A., Freeman, W. T.: Discovering objects and their location in images. In: ICCV. vol. 1, pp. 370-377. IEEE (2005); Kamper, H., Jansen, A., Goldwater, S.: Fully unsupervised small-vocabulary speech recognition using a segmental Bayesian model. In: Interspeech (2015); Lee, H., Pham, P., Largman, Y., Ng, A. Y.: Unsupervised feature learning for audio classification using convolutional deep belief networks. In: Advances in neural information processing systems. pp. 1096-1104 (2009)). These methods conventionally relied on some complementary information provided with the data to improve learning, which may not be available for several classification tasks in medical imaging.

In medical imaging, there have been different approaches that used unsupervised learning for detection and diagnosis problems. The approach by Shin et al. used stacked auto-encoders for multiple organ detection in MRI scans. (Shin, H. C., Orton, M. R., Collins, D. J., Doran, S. J., Leach, M. O.: Stacked autoencoders for unsupervised feature learning and multiple organ detection in a pilot study using 4d patient data. IEEE transactions on pattern analysis and machine intelligence 35(8), 1930-1943 (2013)). Vaidhya et al. presented a brain tumor segmentation method with stacked denoising autoencoder evaluated on multi-sequence MRI images. (Vaidhya, K., Thirunavukkarasu, S., Alex, V., Krishnamurthi, G.: Multi-modal brain tumor segmentation using stacked denoising autoencoders. In: International Workshop on Brainlesion: Glioma, Multiple Sclerosis, Stroke and Traumatic Brain Injuries. pp. 181-194. Springer (2015)). In a work by Sivakumar et al., the segmentation of lung nodules is performed with unsupervised clustering methods. (Sivakumar, S., Chandrasekar, C.: Lung nodule segmentation through unsupervised clustering models. Procedia engineering 38, 3064-3073 (2012)). In another study, Kumar et al. used features from autoencoder for lung nodule classification. (Kumar, D., Wong, A., Clausi, D. A.: Lung nodule classification using deep features in CT images. In: Computer and Robot Vision (CRV), 2015 12th Conference on. pp. 133-138. IEEE (2015)). These auto-encoder approaches, however, did not yield satisfactory classification results. Other than these, unsupervised deep learning has also been explored for mammographic risk prediction and breast density segmentation. (Kallenberg, M., Petersen, K., Nielsen, M., Ng, A.Y., Diao, P., Igel, C., Vachon, C.M., Holland, K., Winkel, R.R., Karssemeijer, N., et al.: Unsupervised deep learning applied to breast density segmentation and mammographic risk scoring. IEEE transactions on medical imaging 35(5), 1322-1331 (2016)).

Unsupervised feature learning remains an active research area for the medical imaging community, more recently with Generative Adversarial Networks (GAN). (Radford, A., Metz, L., Chintala, S.: Unsupervised representation learning with deep convolutional generative adversarial networks. arXiv preprint arXiv:1511.06434 (2015)). In order to explore the information from unlabeled images, Zhang et al. described a semi-supervised method for the classification of four types of nodules. (Zhang, F., Song, Y., Cai, W., Zhou, Y., Fulham, M., Eberl, S., Shan, S., Feng, D.: A ranking-based lung nodule image classification method using unlabeled image knowledge. In: IEEE ISBI. pp. 1356-1359. IEEE (2014)).

In sharp contrast to the above approaches, the unsupervised learning strategies developed by the inventors do not involve feature learning using auto-encoders. Using sets of hand-crafted as well as pre-trained deep learning features, the inventors have developed a new unsupervised learning algorithm where an initially estimated label set is progressively improved via proportion-SVM.

In light of the shortcomings of the current approaches, what is needed is a way to detect nodules, such as lung nodules or IPMNs, from an imaging scan in a single shot using a single-scale network and subsequently to characterize the malignancy of the detected nodule/neoplasm from an imaging scan.

SUMMARY OF INVENTION

The inventors have developed a system and method comprising two complementary technologies for image-based screening and diagnosis of lung cancer from CT scans. The first technology, known as Single Shot Single Scale Lung Nodule Detection (S4ND), is used to screen detection of lung nodules. The second technology, referred to as "MTL-TumorNET", is a network that identifies malignancy of a detected nodule in CT scans and is used for characterizing the nodules as benign or malignant.

For detection of nodules from an imaging scan, current lung nodule detection studies rely on computationally expensive multi-stage frameworks to detect nodules from CT scans. To address this computational challenge and provide better performance, the inventors propose S4ND, a new deep learning-based method for lung nodule detection. The approach uses a single feed forward pass of a single network for detection and provides better performance when compared to the current literature. The whole detection pipeline is designed as a single 3D Convolutional Neural Network (CNN) with dense connections, trained in an end-to-end manner. S4ND does not require any further post-processing or user guidance to refine detection results. Experimentally, the inventors compared the network with the current state-of-the-art object detection network (SSD) in computer vision as well as the state-of-the-art published method for lung nodule detection (3D DCNN). Publicly available 888 CT scans from LUNA challenge dataset were used and showed that the proposed method outperforms the current literature both in terms of efficiency and accuracy by achieving an average FROC-score of 0:897. The inventors also provide an in-depth analysis of the proposed network to shed light on the unclear paradigms of tiny object detection.

With regard to diagnosing malignancy in a detected nodule, risk stratification of cancer tumors in radiology images can be improved with computer-aided diagnosis (CAD) tools which can be made faster and more accurate. Tumor characterization through CADs can enable non-invasive cancer staging and prognosis and foster personalized treatment planning as a part of precision medicine. The inventors propose both supervised and unsupervised machine learning strategies to improve tumor characterization. In the supervised learning method, the inventors demonstrate significant gains in deep learning algorithms, particularly by utilizing a 3D Convolutional Neural Network along with transfer learning. For lung nodule characterization, the inventors present a 3D CNN based supervised learning approach to fully appreciate the anatomical information in 3D, which would be otherwise lost in the conventional 2D approaches. The inventors use a fine-tuning strategy to avoid the requirement for a large number of volumetric training examples for 3D CNN. In order to fine-tune, the inventors use a pre-trained network (trained on 1 million videos) and fine-tune it on the CT data. Motivated by the radiologists' interpretations of the scans, the inventors introduce a graph regularized sparse Multi-Task Learning (MTL) platform to integrate the complementary features from lung nodule attributes to improve malignancy prediction. The inventors were able to achieve high-level lung nodule attributes having varying levels of prominence.

In the unsupervised learning method, the inventors developed an unsupervised scheme to address the limited availability of labeled training data, a common problem in medical imaging applications. Inspired by learning from label proportion (LLP) approaches, the inventors developed a new algorithm, proportion-SVM (aSVM), to characterize tumor types. In the proposed unsupervised learning algorithm, instead of hard assigning labels, the inventors estimate the label proportions in a data-driven manner. To alleviate the effect of noisy labels (i.e. mislabeling) obtained during clustering, aSVM is employed, which is trained on label proportions only.

The inventors evaluated the proposed supervised and unsupervised learning algorithms to determine the characterization of lung nodules and IPMN cysts. In the era where the wave of deep learning has swept into almost all domains of visual analysis, the contribution of features extracted from different deep learning architectures was investigated and it is believed that this is the first work to investigate the automatic diagnosis of IPMNs from MRI. Both the supervised and unsupervised methods developed by the inventors were evaluated on two different types of tumors: lung and pancreas with 1018 CT and 171 MRI scans respectively.

In an embodiment, a method of detecting and diagnosing cancer characterized by the presence of at least one nodule in a subject is presented comprising: providing an imaging scan of the subject; automatically detecting presence of the at least one nodule in the imaging scan using a 3D convolutional neural network (CNN) having convolution blocks with dense connections wherein a cell-wise classification of input is done in a single feed forward path of the CNN in one shot to detect all the nodules in a given volume simultaneously; and automatically determining a classification of malignancy of the at least one detected nodule in the imaging scan using a supervised or an unsupervised deep learning method.

The supervised learning method may be comprised of the steps of: automatically determining imaging attributes of the at least one nodule using transfer learning of a pre-trained 3D convolutional neural network (C3D); fine-tuning the C3D network with binary labels for malignancy and the imaging attributes; and incorporating the malignancy binary label and the binary labels for the imaging attributes of the at least one nodule into a graph regularized sparse multi-task learning (MTL) framework to obtain the classification of malignancy of the at least one nodule. The unsupervised learning method may be comprised of the steps of: performing clustering on the imaging attributes of the at least one nodule to estimate an initial set of labels; computing label proportions corresponding to each cluster; and training a classifier using the label proportions and clusters to obtain the classification of malignancy of the at least one nodule.

With regard to the detection step of the method described herein, the input refers to the imaging scan. The input to the 3D CNN of the detection step may be a 512×512×8 volume. The output of the 3D CNN of the detection step may be a 16×16×8 probability map representing likelihood of nodule presence. The 3D CNN of the detection step may be comprised of the following: a total of 36 3D convolution layers wherein 6 convolution layers form each of 5 dense blocks and remaining convolution layers form transition layers; 4 max-pooling layers; 4 transition layers; and a sigmoid activation function.

With regard to the determination of malignancy (diagnosing) step, the imaging attributes are selected from the group consisting of calcification, speculation, sphericity, lobulation, margin, texture and combinations thereof. In some embodiments, all 6 imaging attributes are used in the method. The classifier of the unsupervised learning method of the diagnosing step may be proportion-support vector machine (aSVM).

The cancer may be lung cancer or pancreatic cancer. The imaging scan may be created using computed tomography (CT), magnetic resonance imaging (MRI), positron emission tomography (PET), positron emission tomography/computed tomography (PET/CT), positron emission tomography/magnetic resonance imaging (PET/MRI) or contrast-enhanced ultrasound (CEUS).

In another embodiment, a method of detecting and diagnosing lung cancer in a subject is presented comprising: providing a computed tomography (CT) scan of the subject; and automatically detecting presence of at least one nodule in the CT scan using a 3D convolutional neural network (CNN) having convolution blocks with dense connections wherein a cell-wise classification of input is done in a single feed forward path of the CNN in one shot to detect all the nodules in a given volume simultaneously.

The 3D CNN may be comprised of a total of 36 3D convolution layers wherein 6 convolution layers form each of 5 dense blocks and remaining convolution layers form transition layers; 4 max-pooling layers; 4 transition layers; and a sigmoid activation function.

The method may be further comprised of the step of automatically determining a classification of malignancy of the at least one detected nodule in the imaging scan using a supervised deep learning method wherein the supervised deep learning method may be comprised of the steps of: automatically determining imaging attributes of the at least one nodule using transfer learning of a pre-trained 3D convolutional neural network (C3D); fine-tuning the C3D network with binary labels for malignancy and the imaging attributes; and incorporating the malignancy binary label and the binary labels for the imaging attributes of the at least one nodule into a graph regularized sparse multi-task learning (MTL) framework to obtain the classification of malignancy of the at least one nodule. The imaging attributes may be selected from the group consisting of calcification, speculation, sphericity, lobulation, margin, texture and combinations thereof.

Alternatively, the method may be further comprised of the step of automatically determining a classification of malignancy of the at least one detected nodule in the imaging scan using an unsupervised deep learning method wherein the unsupervised deep learning method may be comprised of the steps of: performing clustering on the imaging attributes of the at least one nodule to estimate an initial set of labels; computing label proportions corresponding to each cluster; and training a classifier using the label proportions and clusters to obtain the classification of malignancy of the at least one nodule. The imaging attributes may be selected from the group consisting of calcification, speculation, sphericity, lobulation, margin, texture and combinations thereof. The classifier of the unsupervised learning method of the diagnosing step may be proportion-support vector machine (aSVM).

In a further embodiment, a method of detecting and diagnosing pancreatic cancer in a subject is presented comprising: providing an imaging scan of the subject; automatically detecting presence of the at least one neoplasm in the imaging scan using a 3D convolutional neural network (CNN) having convolution blocks with dense connections wherein a cell-wise classification of input is done in a single feed forward path of the CNN in one shot to detect all the neoplasm in a given volume simultaneously; and automatically determining a classification of malignancy of the at least one detected neoplasm in the imaging scan using a supervised or an unsupervised deep learning method. The imaging scan may be a magnetic resonance image (MRI) scan or a CT scan.

The supervised learning method may be comprised of the steps of: automatically determining imaging attributes of the at least one neoplasm using transfer learning of a pre-trained 3D convolutional neural network (C3D); fine-tuning the C3D network with binary labels for malignancy and the imaging attributes; and incorporating the malignancy binary label and the binary labels for the imaging attributes of the at least one neoplasm into a graph regularized sparse multi-task learning (MTL) framework to obtain the classification of malignancy of the at least one neoplasm. Alternatively, the unsupervised learning method may be comprised of the steps of: performing clustering on the imaging attributes of the at least one neoplasm to estimate an initial set of labels; computing label proportions corresponding to each cluster; and training a classifier using the label proportions and clusters to obtain the classification of malignancy of the at least one neoplasm. The imaging attributes may be selected from the group consisting of calcification, speculation, sphericity, lobulation, margin, texture and combinations thereof.

The classifier of the unsupervised learning method of the diagnosing step may be proportion-support vector machine (αSVM).

The 3D CNN of the diagnosing step may be comprised of a total of 36 3D convolution layers wherein 6 convolution layers form each of 5 dense blocks and remaining convolution layers form transition layers; 4 max-pooling layers; 4 transition layers; and a sigmoid activation function.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which:

FIG. 8A-B is a series of images depicting the influence of deep learning features obtained from different layers of a VGG network with and without ReLU non-linearities. (A) graph depicting accuracy, sensitivity and specificity for unsupervised lung nodule classification (clustering); (B) graph depicting accuracy, sensitivity and specificity for IPMN classification (clustering);

DETAILED DESCRIPTION OF THE PREFERRED EMBODIMENT

Figure 1:
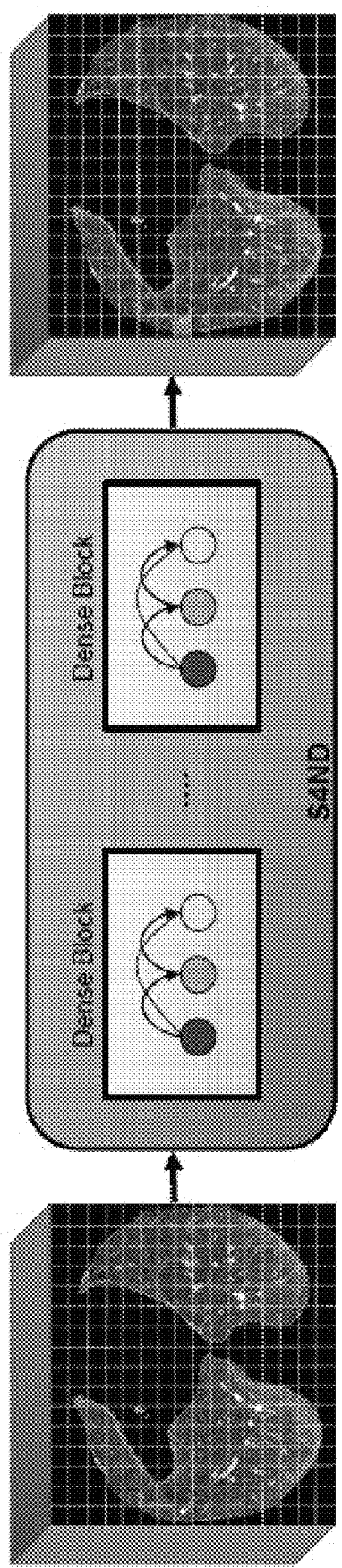
FIG. 1 is an image depicting the S4ND framework which models nodule detection as a cellwise classification of the input volume. The input volume is divided by a 16×16×8 grid and is passed through a newly designed 3D dense CNN. The output is a probability map indicating the presence of a nodule in each cell.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supersedes any disclosure of an incorporated publication to the extent there is a contradiction.

Abbreviation List
ANN—Artificial Neural Networks
CAD—Computer Aided Diagnosis
CNN—Convolutional Neural Network
CPM—Competition Performance Metric
CT—Computerized Tomography
GA—Genetic Algorithm
GAN—Generative Adversarial Networks
IPMN—Intraductal Papillary Mucinous Neoplasms
LBP—Local Binary Patterns
LDA—Linear Discriminant Analysis
MIL—Multiple Instance Learning
MIll—Magnetic Resonance Imaging
MTL—Multi-Task Learning
PET—Positron Emission Tomography
ReLU—Rectifier Linear Unit
RF—Random Forests
ROI—Region of Interest
RSM—Random Subspace Method
SSD—Single-Shot Multi-Box Object Detection
SVM—Support Vector Machine
Definitions Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supersedes any disclosure of an incorporated publication to the extent there is a contradiction.

As used in the specification and claims, the singular form "a", "an" and "the" include plural references unless the context clearly dictates otherwise.

As used herein, the term "comprising" is intended to mean that the products, compositions and methods include the referenced components or steps, but not excluding others. "Consisting essentially of" when used to define products, compositions and methods, shall mean excluding other components or steps of any essential significance. "Consisting of" shall mean excluding more than trace elements of other components or steps.

"Subject" is used to describe an animal, preferably a mammal, more preferably a human, on whom the present system and method are used.

The term "about" as used herein is not intended to limit the scope of the invention but instead encompass the specified material, parameter or step as well as those that do not materially affect the basic and novel characteristics of the invention. In some instances, the term "about" refers to +10%.

"Computer aided diagnosis (CAD)" as used herein refers to a system and method of use thereof for detecting and determining risk stratification of lung nodules or IPMN from an imaging scan such as a CT scan or an MRI scan. This system is comprised of two main modules each having a series of steps utilizing various algorithms/equations. The first module consists of steps for detecting lung nodules or IPMN in a single shot. The second module consists of steps for determining the risk stratification of the lung nodule or IPMN, i.e. determining malignancy using either a supervised approach or an unsupervised approach. Depending on the specific purpose, the modules can operate independently or in combination with each other. While the invention is described with respect to lung nodules and IPMN, detection and risk stratification of other types of cancerous nodules are contemplated by the invention.

"Imaging scan" as used herein refers to a detailed scan or image of the body of a mammal that is obtained using technology such as X-rays, radio waves, magnetic fields, scanners, radiopharmaceuticals, and/or high frequency sound waves. Examples of such scans include, but are not limited to positron emission tomography (PET) scans; computed tomography (CT) scans; magnetic resonance imaging (MRI) scans; positron emission tomography/computed tomography (PET/CT) scans; positron emission tomography/magnetic resonance imaging (PET/MRI) scans; and contrast-enhanced ultrasound (CEUS) scans.

"Cancer" as used herein refers to a physiological condition in mammals that is typically characterized by unregulated cell growth. Specifically, as described herein, the term "cancer" refers to those cancers characterized by nodules or solid tumors. Leukemias are excluded from the instant definition as they do not produce a solid tumor. Examples of cancers that can be detected and diagnosed by the instant invention include, but are not limited to, sarcomas; carcinomas; lymphomas; lung cancers; pancreatic cancer; breast cancer; prostate cancer; testicular cancer; ovarian cancer; bladder cancer; cervical cancer; colorectal cancer; thyroid cancer; brain cancers; spleen cancer; stomach cancer; gastrointestinal cancers; head and neck carcinoma; bone cancers; colon cancer; esophageal cancer; endometrial cancer; uterine cancer; skin cancers including squamous cell carcinoma and melanoma; epithelial carcinoma; glioma; astrocytoma; medulloblastoma; craniopharyngioma; ependymoma; pinealoma; hemangioblastoma; acoustic neuroma; oligodendroglioma; meningioma; neuroblastoma; retinoblastoma; multiple myeloma; renal cell carcinoma; hepatocellular carcinomas: gastric cancers; lymphoma: fibrosarcoma; myosarcoma; liposarcoma; chondrosarcoma; osteogenic sarcoma; chordoma; angiosarcoma; endotheliosarcoma; lymphangiosarcoma; lymphangioendotheliosarcoma; synovioma; mesothelioma; Ewing's tumor; leiomyosarcoma; rhabdomyosarcom; urothelial carcinoma; basal cell carcinoma; adenocarcinoma; sweat gland carcinoma; sebaceous gland carcinoma; papillary carcinoma; papillary adenocarcinomas; cystadenocarcinoma; medullary carcinoma; bronchogenic carcinoma; renal cell carcinoma; hepatoma; bile duct carcinoma; choriocarcinoma; a seminoma; an embryonal carcinoma; Wilms' tumor; gallbladder cancer; laryngeal cancer; oral cancer; and soft tissue sarcoma. While the invention is described with respect to lung nodules (lung cancer) and IPMN (pancreatic cancer), other cancers characterized by solid tumors are contemplated.

"Nodule" or "neoplasm" as used herein refers to an abnormal growth of tissue or aggregation of cells in the body. Nodules may be benign or malignant. In some cases, the term "tumor" is used synonymously with "nodule" or "neoplasm".

"Imaging attributes" as used herein refers to the appearance characteristics of the nodule or neoplasm. Examples of imaging attributes used in the instant invention include, but are not limited to, calcification, speculation, sphericity, lobulation, margin, and texture.

In Example 1, the inventors have developed a method of detecting lung nodules in a single shot. The method uses deep learning and a single feed forward pass of a single network for detection of lung nodules.

In Examples 2 and 3, the inventors present a framework for the malignancy determination of lung nodules with 3D CNN based graph regularized sparse MTL. This is the first work where transfer learning is studied and empirically analyzed for 3D deep networks so as to improve risk stratification. Usually, the data sharing for medical imaging is highly regulated and the accessibility of experts (radiologists) to label these images is limited. As a consequence, the access to the crowdsourced and publicly gathered and annotated data such as videos may help in obtaining discriminative features for medical image analysis.

The inventors analyzed the significance of different imaging attributes corresponding to lung nodules including spiculation, texture, calcification and others for risk assessment. Instead of manually modeling these attributes, a 3D CNN was used to learn rich feature representations associated with these attributes. The graph regularized sparse MTL framework was employed to integrate 3D CNN features from these attributes. The features associated with these attributes were found to be complementary to those corresponding to malignancy.

In Example 3, the inventors explored the potential of unsupervised learning for malignancy determination. Since in most medical imaging tasks radiologists are required to get annotations, acquiring labels to learn machine learning models is more cumbersome and expensive as compared to other computer vision tasks. In order to address this challenge, clustering was employed to obtain an initial set of labels and progressively refined them with aSVM. The proposed approach outperformed the other methods in evaluation metrics.

Following up on the application of deep learning for almost all tasks in the visual domain, the influence of different pre-trained deep networks for lung nodule classification was studied. In some instances, commonly used imaging features, such as GIST, have comparable results as those obtained from pre-trained network features. This observation can be explained by the fact that the deep networks were trained on ImageNet classification tasks so the filters in CNN were more tuned to the nuances in natural images as compared to medical images.

The inventors evaluated the proposed supervised and unsupervised learning algorithms on two different tumor diagnosis challenges: lung and pancreas with 1018 CT and 171 MRI scans, respectively, and obtained the state-of-the-art sensitivity and specificity results in both problems.

With regard to pancreatic tumors, this is both the first and the largest evaluation of a CAD system for IPMN classification. CAD systems for IPMN classification are relatively newer research problems and there is a need to explore the use of different imaging modalities to improve classification. Although MRI remains the most common modality to study pancreatic cysts, CT images can also be used as a complementary imaging modality due to its higher resolution and its ability to capture smaller cysts. Additionally, a combination of T2-weighted, contrast-enhanced and unenhanced T1-weighted sequences can help improve detection and diagnosis of IPMN. (Sivic, J., Russell, B. C., Efros, A. A., Zisserman, A., Freeman, W. T.: Discovering objects and their location in images. In: ICCV. vol. 1, pp. 370-377. IEEE (2005)). In this regard, multi-modal deep learning architectures can be deemed useful. (Chatfield, K., Simonyan, K., Vedaldi, A., Zisserman, A.: Return of the devil in the details: Delving deep into convolutional nets. In: British Machine Vision Conference (2014)). The detection and segmentation of the pancreas can also be useful to make a better prediction about the presence of IPMN and cysts. Due to its anatomy, the pancreas is a challenging organ to segment, particularly in MRI images. To address this challenge, other imaging modalities can be utilized for joint segmentation and diagnosis of pancreatic cysts and IPMN. Furthermore, visualization of activation maps can be quite useful for the clinicians to identify new imaging biomarkers that can be employed for diagnosis in future.

Example 1

Nodule Detection in a Single Shot

Current lung nodule detection studies rely on computationally expensive multi-stage frameworks to detect nodules from CT scans. To address this computational challenge and provide better performance, the inventors have developed a new deep learning-based method for lung nodule detection termed S4ND. The approach uses a single feed forward pass of a single network for detection and provides better performance when compared to the current literature. The whole detection pipeline is designed as a single 3D Convolutional Neural Network (CNN) with dense connections, trained in an end-to-end manner. S4ND does not require any further post-processing or user guidance to refine detection results. The inventors compared the network with the current state of the art object detection network (SSD) in computer vision as well as the state-of-the-art published method for lung nodule detection (3D DCNN). Using publicly available 888 CT scans from the LUNA challenge dataset, the inventors showed that the proposed method outperforms the current literature both in terms of efficiency and accuracy by achieving an average FROC score of 0.897. The inventors provide an in-depth analysis of the proposed network to shed light on the unclear paradigms of tiny object detection.

While this example is described with respect to lung nodules, the method may be used to detect any potentially cancerous nodules such as intraductal papillary mucinous neoplasms (IPMN) which are indicative of pancreatic cancer. Additionally, other imaging scans may be used in the method including, but not limited to, positron emission tomography (PET) scans; computed tomography (CT) scans; magnetic resonance imaging (MRI) scans; positron emission tomography/computed tomography (PET/CT) scans; positron emission tomography/magnetic resonance imaging (PET/MRI) scans; and contrast-enhanced ultrasound (CEUS) scans.

Methods

FIG. 1 illustrates an overview of the proposed method for lung nodule detection in a single shot. The input to the network is a 3D volume of a lung CT scan. The proposed 3D densely connected Convolutional Neural Network (CNN) divides the input volume into a grid of size S×S×T cells. The inventors model lung nodule detection as a cell-wise classification problem, done simultaneously for all the cells. Unlike commonly used region proposal networks, the proposed network is able to reason the presence of nodule in a cell using global contextual information, based on the whole 3D input volume.

Single-Scale Detection

As opposed to object detection in natural scenes, the inventors show that lung nodule detection can be performed efficiently and with high accuracy in a single scale. Current literature reports the most frequently observed nodule sizes fall within 3 mms to 32 mms, most of which are less than 9 mm and are considered as small, as defined by the American Thoracic Society. (Setio, A.A.A., et al., Validation, comparison, and combination of algorithms for automatic detection of pulmonary nodules in computed tomography images: The luna16 challenge. Medical Image Analysis 42(Supplement C), 1-13 (2017)). Nodules less than 3 mm in size are the most difficult to detect due to their tiny nature and high similarities to vessels. Based on the statistics of nodule size and the evidence in literature, the inventors hypothesize that a single scale framework with the grid size that the inventors defined (16×16×8 leading to the cell sized of 32×32×8 on a volume of size 512×512×8) is sufficient to fit all the expected nodule sizes and provide good detection results without the need to increase the algorithmic complexity to multi-scale. This has been partially proven in other multi-scale studies. (Dou, Q., Chen, H., Yu, L., Qin, J., Heng, P. A.: Multilevel contextual 3-d cnns for false positive reduction in pulmonary nodule detection. IEEE Transactions on Biomedical Engineering 64(7), 1558-1567 (2017)).

Dense and Deeper Convolution Blocks Improve Detection

The loss of low-level information throughout a network causes either a high number of false positives or low sensitivity. One efficient way that helps the flow of information in a network and keeps this low-level information, combining it with the high-level information, is the use of dense connections inside the convolution blocks. The inventors empirically show that deeper densely connected blocks provide better detection results. This, however, comes with the cost of more computation. In the experiments the inventors found that dense blocks with 6 convolution layers provide a good balance of detection accuracy and computational efficiency.

Max-Pooling Improves Detection

As the inventors go deeper in a CNN, it is desired to pick the most descriptive features and pass only those to the next layers. Recently, architectures for object detection in natural images preferred the use of convolutions with stride 2 instead of pooling. (Liu, W., Anguelov, D., Erhan, D., Szegedy, C., Reed, S., Fu, C. Y., Berg, A. C.: Ssd: Single shot multibox detector. In: European conference on computer vision. pp. 21-37. Springer (2016)). In the context of tiny object detection, this feature reduction plays an important role. Since the objects of interest are small, if the inventors carelessly pick the features to propagate, the inventors can easily lose the objects of interest through the network and end up with a sub-optimal model. In theory, the goal is to have as less pooling as possible. Also, it is desired to have this feature sampling step in a way that information loss is minimized. There are multiple approaches for sampling information through the network. Average pooling, max pooling and convolutions with stride 2 are some of the options. In the experiments, the inventors showed that max pooling is the best choice of feature sampling for the task as it selects the most discriminative feature in the network. Also, the inventors showed that convolution layers with stride of 2 are performing better compared to average pooling. The reason is that convolution with stride 2 is very similar in its nature to weighted averaging with the weights being learned in a data driven manner.

Proposed 3D Deep Network Architecture

The network architecture consists of 36, 3D convolution layers, 4 max-pooling layers and a sigmoid activation function at the end. 30 of convolution layers form 5 blocks with dense connections and without pooling, which enhance low-level information along with high-level information, and the remainder form the transition layers. The details of the architecture can be seen in FIG. 2. The input to the network is 512×512×8 and the output is a 16×16×8 probability map. Each cell in the output corresponds to a cell of the original image divided by a 16×16×8 grid and decides whether there is a nodule in that cell or not.

Figure 2:
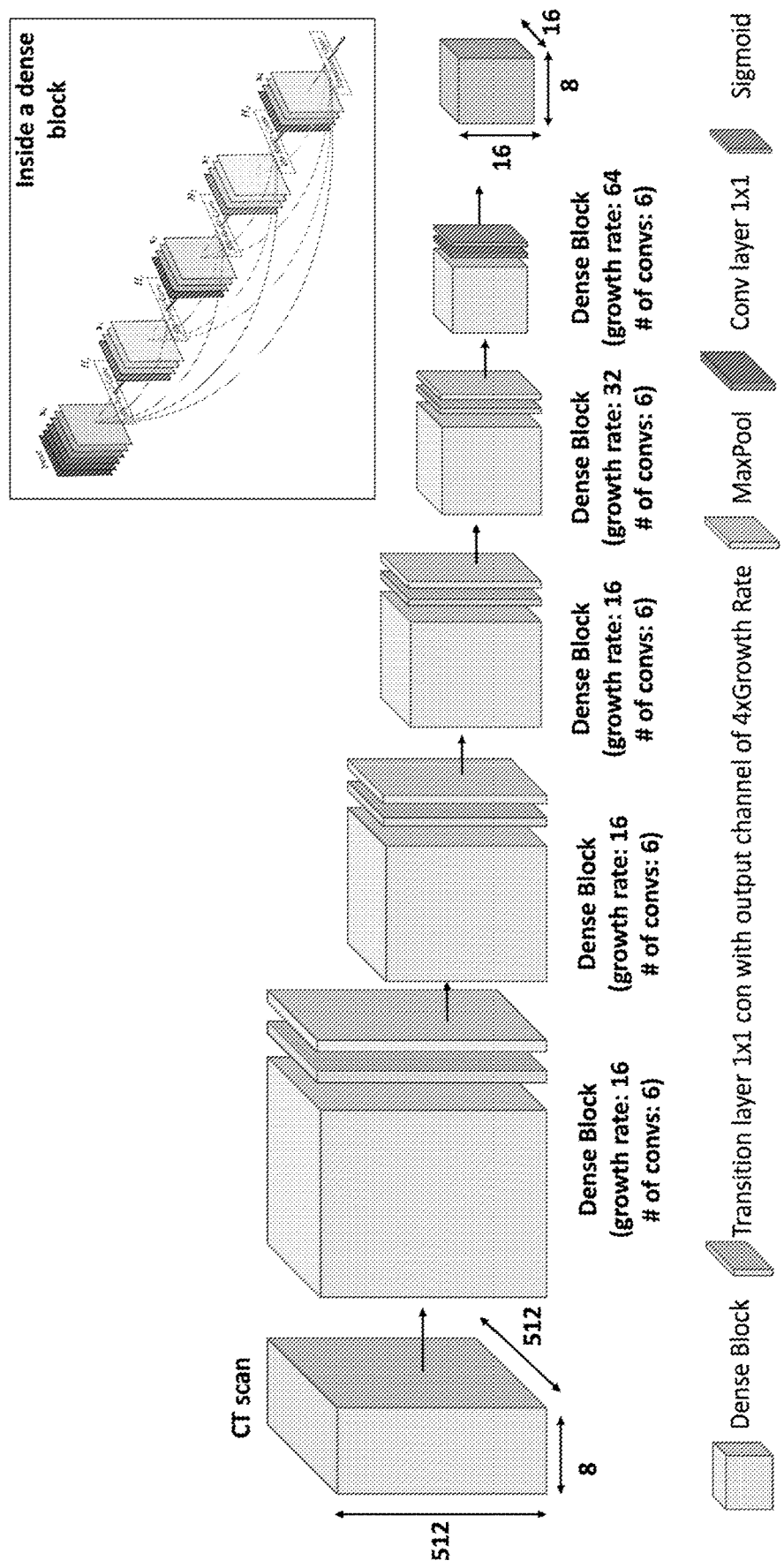
FIG. 2 is an image depicting input to the network is a 512×512×8 volume and output is a 16×16×8 probability map representing likelihood of nodule presence. The network has 5 dense blocks, each having 6 cony. Layers. The growth rates of blocks 1 to 5 is 16, 16, 16, 32, 64 respectively. The network has 4 transition layers and 4 max-pooling layers. The last block is followed by a convolution layer with kernel size 1×1×1 and output channel of 1 and a sigmoid activation function.

Densely connected convolution blocks: As stated, the network consists of 5 densely connected blocks, each block containing 6 convolution layers with an output channel of g, which is the growth rate of that block. Inside the blocks, each layer receives all the preceding layers' feature maps as inputs. FIG. 2 (top right) illustrates the layout of a typical dense block. Dense connections help the flow of information inside the network. Assume $x_0$ is the input volume to the block and $x_i$ is the output feature map of layer i inside the block. Each layer is a non-linear function $F_i$, which in the case is a composition of convolution, batch normalization (BN) and rectifier linear unit (ReLU). With dense connections, each layer receives a concatenation of all previous layers' feature maps as input $x_i = F_i([x_0, x_1, \ldots, x_{i-1}])$, where $x_i$ is the output feature map from layer i and $[x_0, x_1, \ldots, x_{i-1}]$ is the channel-wise concatenation of previous layers' feature maps.

Growth rate (GR): is the number of feature maps that each layer $F_i$ produces in the block. This number is fixed for each block, but it can change from one block to the other. Assume the number of channels in the input layer of a block is $c_0$ and the block has i convolution layers with a growth rate of g. Then the output of the block will have $c_0 + (i \cdot 1)g$ channels.

Transition layers: as can be seen in the above formulations, the number of feature maps inside each dense block increases dramatically. Transition layers are 1×1×1 convolution layers with 4 g output channels, where g is the growth rate of previous block. Using a convolution with kernel size of 1×1×1 compresses the information channel-wise and reduces the total number of channels throughout the network.

Training the network: The created ground truths for training the network are 3D volumes with size 16×16×8. Each element in this volume corresponds to a cell in the input image and has label 1 if a nodule exists in that cell and 0 otherwise. The design of the network allows for an end-to-end training. The inventors model detection as a cell wise classification of input which is done in one feed forward path of the network in one shot. This formulation detects all the nodules in the given volume simultaneously. The loss function for training the network is weighted cross-entropy defined as:

$$L(Y^{(n)}, f(X^{(n)})) = \sum_{i=1}^{k_n} -y_i \log(f(x_i)), \quad (1)$$

where Y s are the labels and Xs are the inputs.

Experiments and Results

Data and evaluation: To evaluate detection performance of S4ND, the inventors used Lung Nodule Analysis (LUNA16) Challenge dataset (consisting of a total of 888 chest CT scans, slice thickness<2.5 mm, with ground truth nodule locations). For the training, the inventors performed a simple data augmentation by shifting the images in 4 directions by 32 pixels. The inventors sampled the 3D volumes for training so that nodules appear in random locations to avoid bias toward location of nodules. The inventors performed 10-fold cross validation to evaluate the method by following the LUNA challenge guidelines. Free-Response Receiver Operating Characteristic (FROC) analysis has been conducted to calculate sensitivity and specificity. (Kundel, H., Berbaum, K., Dorfman, D., Gur, D., Metz, C., Swensson, R.: Receiver operating characteristic analysis in medical imaging. ICRU Report 79(8), 1 (2008)). Suggested by the challenge organizers, sensitivity at 7 FP/scan rates (i.e. 0.125, 0.25, 0.5, 1, 2, 4, 8) was computed. The overall score of system (Competition Performance Metric-CPM) was defined as the average sensitivity for these 7 FP/scan rates.

Building blocks of S4ND and comparisons: This subsection explains how the inventors build the proposed S4ND network and provides a detailed comparison with several baseline approaches. The inventors compared performance of S4ND with state-of-the-art algorithms, including SSD (single-shot multi-box object detection, known to be very effective for object detection in natural scenes. (Liu, W., Anguelov, D., Erhan, D., Szegedy, C., Reed, S., Fu, C.Y., Berg, A.C.: Ssd: Single shot multibox detector. In: European conference on computer vision. pp. 21-37. Springer (2016)). The inventors showed that SSD suffers from low performance in lung nodule detection, even though trained from scratch on LUNA dataset. A high degree of scale bias and known difficulties of the lung nodules detection (texture, shape, etc.) in CT data can be considered as potential reasons. To address this poor performance, the inventors propose to replace the convolution layers with dense blocks to improve the information flow in the network. Further, the inventors experimentally tested the effects of various down sampling techniques. Table 1 shows the results of different network architectures along with the number of parameters based on these combinations. The inventors implemented the SSD based architecture with 3 different pooling strategies: (1) average pooling (2D Dense Avepool), (2) replacing pooling layers with convolution layers with kernel size 3 3 and stride 2 (2D Dense Nopool) and (3) max pooling (2D Dense Maxpool). The experiments show that max pooling is the best choice of feature sampling for tiny object detection as it selects the most discriminating feature in each step. 2D Dense Nopool outperforms the normal average pooling (2D Dense Avepool) as it is in concept a learnable averaging over 3×3 regions of the network, based on the way the inventors defined kernel size and stride.

TABLE 1

Comparison of different models with varying conditions

| | MODEL | SENSITIVITY % | NUM OF PARAMETERS | CPM |
|---|---|---|---|---|
| RANDOMLY SELECTED 1-FOLD | 2D SSD | 77.8% | 59,790,787 | 0.649 |
| | 2D DENSE AVEPOOL | 84.8% | 67,525,635 | 0.653 |
| | 2D DENSE NOPOOL | 86.4% | 70,661,955 | 0.658 |
| | 2D DENSE MAXPOOL | 87.5% | 67,525,635 | 0.672 |
| | 3D DENSE | 93.7% | 694,467 | 0.882 |
| | 3D INCREASING GR | 95.1% | 2,429,827 | 0.890 |
| | 3D DEEPER BLOCKS | 94.2% | 1,234,179 | 0.913 |
| | PROPOSED (S4ND) | 97.2% | 4,572,995 | 0.931 |
| 10-FOLD | 3D DCNN | 94.6% | 11,720,032 | 0.891 |
| | PROPOSED (S4ND) | 95.2% | 4,572,995 | 0.897 |

Figure 3:
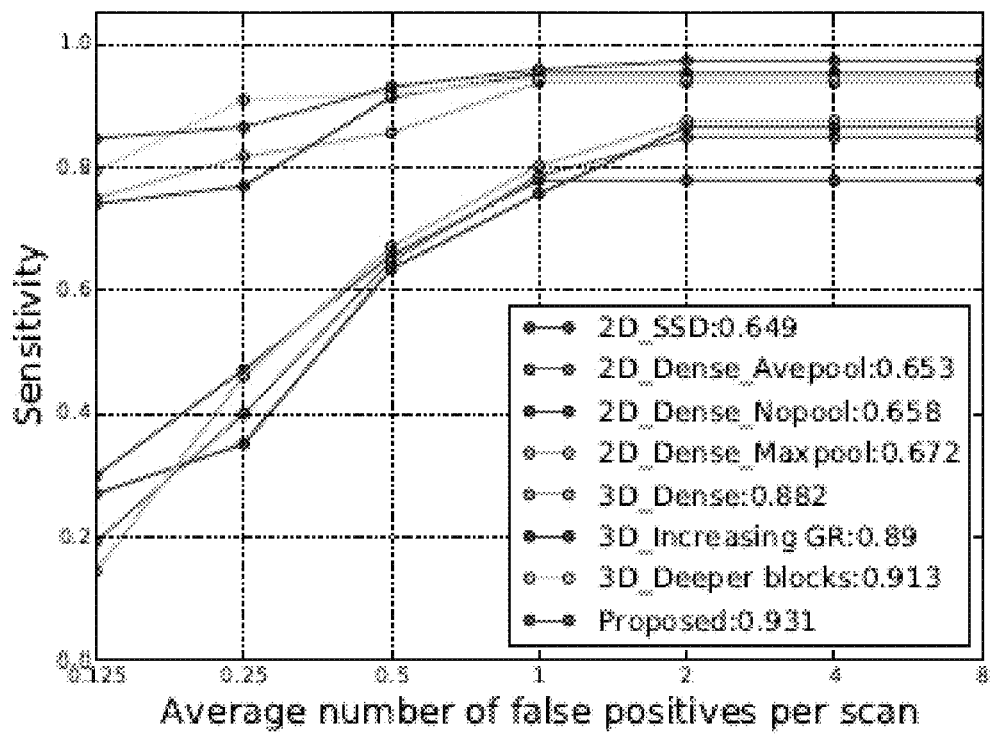
FIG. 3 is a series of graphs depicting a comparison of baseline as well as a comparison with the state of the art. Numbers in front of each method in the legend show Competition Performance Metric (CPM).
Figure 3:
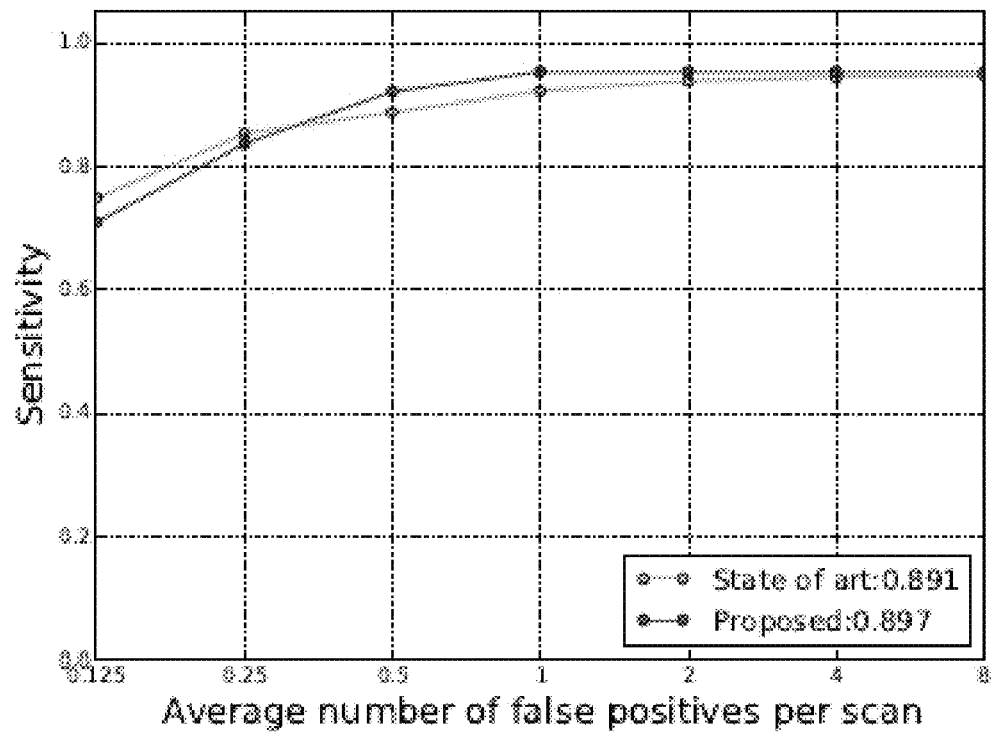
Figure 4:
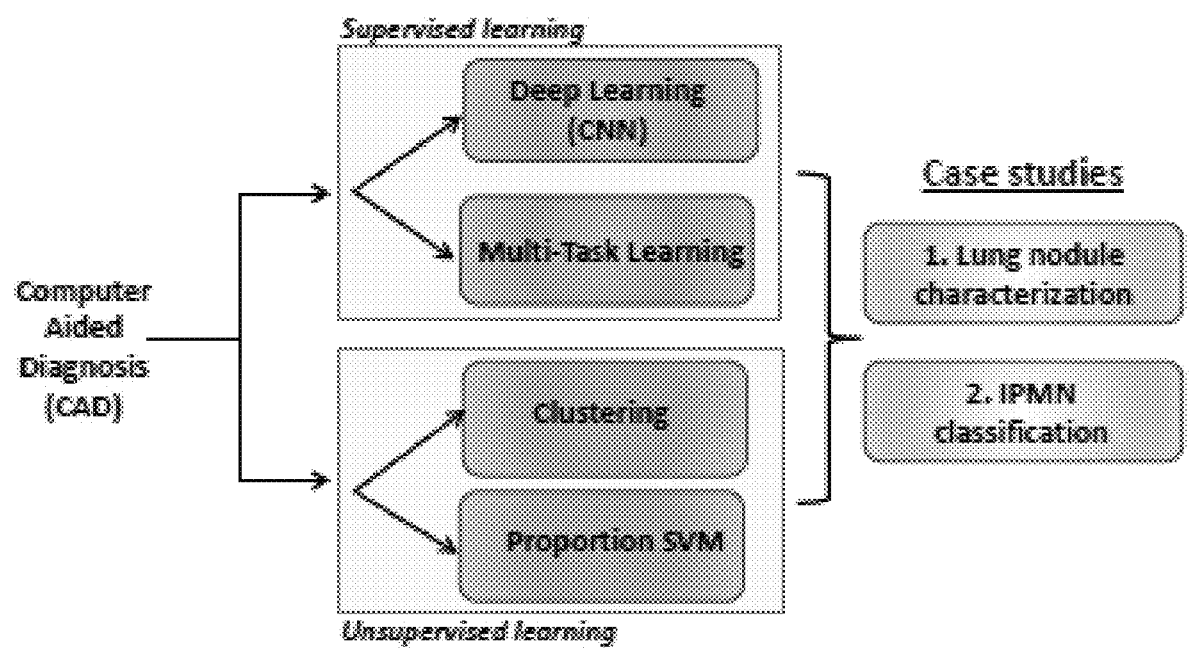
FIG. 4 is a block diagram representing different schemes, methods and experimental case studies. The inventors developed both supervised and unsupervised learning algorithms to characterize tumors. For the supervised learning scheme, a new 3D CNN architecture based on a Graph Regularized Sparse Multi-Task Learning was developed with evaluations being performed for lung nodule characterization from CT scans. For the unsupervised learning scheme, a new clustering algorithm, a SVM, was tested for the categorization of lung nodules from CT scans and pancreatic cysts (IPMN) from MRI cases.

3D Networks, growth rate (GR), and comparisons: The inventors implemented S4ND in a completely 3D manner. Growth rate for all the blocks inside the network was initially fixed to 16 (3D Dense). However, the inventors observed that increasing the growth rate in the last 2 blocks of the network, where the computational expense is lowest, (from 16 to 32 and 64, respectively) improved the performance of detection (3D Increasing GR in Table 1). Also, having deeper blocks, even with a fixed growth rate of 16 for all the blocks, help the information flow in the network and improved the results further (3D Deeper Blocks in Table 1). The final proposed method benefits from both deeper blocks and increasing growth rate in its last two blocks. FIG. 3 (left) shows the FROC comparison of proposed method with the baselines. The 10-fold cross validation results were compared with the current state of the art lung nodule detection method (3D DCNN which is the best published results on LUNA dataset). (Ding, J., Li, A., Hu, Z., Wang, L.: Accurate pulmonary nodule detection in computed tomography images using deep convolutional neural networks. In: International Conference on Medical Image Computing and Computer-Assisted Intervention. pp. 559-567. Springer (2017)). The proposed method outperformed the best available results both in sensitivity and FROC score, while only using as less as a third of its parameters, and without the need for multi-stage refinements.

Major findings: (1) The inventors obtained 0.897 FROC rate in 10-fold cross validation, and consistently outperformed the state-of-the-art methods as well as other alternatives. (2) SSD (the state of the art for object detection in natural images) resulted in the lowest accuracy in all experiments. Proposed S4ND, on the other hand, showed that single scale single shot algorithm performs better and more suited to tiny object detection problem. (3) The proposed method achieved better sensitivity, specificity, and CPM in single fold and 10-fold throughout experiments where S4ND used less than the half parameters of 3D DCNN (current state of the art in lung nodule detection). (4) A careful organization of the architecture helps avoiding computationally heavy processing. The inventors have shown that maxpooling is the best choice of feature selection throughout the network amongst current available methods. (5) Similarly, dense and deeper connections improve the detection rates through better information flow through layers. It should be noted that the runtime of the algorithm for the whole scan, on the test phase, varies from 11 secs to 27 secs based on the number of slices in the scan on a single NVIDIA TITAN Xp GPU workstation with RAM of 64 GBs.

Conclusion

The inventors have developed a single-shot single-scale fast nodule detection algorithm without the need for additional FP removal and user guidance for refinement of detection process as detailed in the experiments conducted on lung nodules. The proposed deep network structure is fully 3D and densely connected. The inventors also critically analyzed the role of densely connected layers as well as maxpooling, average pooling and fully convolutional down sampling in detection process. The inventors present a fundamental solution to address the major challenges of current region proposal-based lung nodule detection methods: candidate detection and feature resampling stages. The inventors experimentally validated the proposed network's performance both in terms of accuracy (high sensitivity/specificity) and efficiency (less number of parameters and speed) on a publicly available LUNA data set, with extensive comparison with the natural object detector networks as well as the state-of-the-art lung nodule detection methods.

Example 2

Tumor Characterization Using Supervised Learning

Risk stratification (characterization) of tumors from radiology images can be more accurate and faster with computer-aided diagnosis (CAD) tools. Tumor characterization through such tools can also enable non-invasive cancer staging, prognosis, and foster personalized treatment planning as a part of precision medicine. Tumor characterization based on supervised learning demonstrates significant gains with deep learning algorithms, particularly by utilizing a 3D Convolutional Neural Network and Transfer Learning. Motivated by the radiologists' interpretations of the scans, the inventors illustrate how to incorporate task dependent feature representations into a CAD system via a graph-regularized sparse Multi-Task Learning (MTL) framework.

The inventors have developed a novel supervised learning strategy to perform risk-stratification of lung nodules from low-dose CT scans. For this strategy, a 3D CNN based discriminative feature extraction is performed from radiology scans. 3D networks are important for the characterization of lung nodules in CT images which are inherently 3-dimensional. The use of conventional 2D CNN methods leads to the loss of vital volumetric information which can be crucial for precise risk assessment of lung nodules. In the absence of a large number of labeled training examples, the inventors utilized a pre-trained 3D CNN architecture and fine-tuned the network with a lung nodules dataset. Also, inspired by the significance of lung nodule attributes for clinical determination of malignancy, the inventors utilized the information about six high-level nodule attributes such as calcification, spiculation, sphericity, lobulation, margin, and texture to improve automatic benign-malignant classification. (Results shown in FIG. 5A). These high-level features are subsequently integrated into a novel graph regularized multi-task learning (MTL) framework to yield the final malignancy output. The impact of the aforementioned lung nodule attributes was analyzed in-depth for malignancy determination and these attributes were found to be complementary when obtaining the malignancy scores. From a technical perspective, the inventors also exploited different regularizers and multi-task learning approaches such as trace-norm and graph regularized MTL for regression.

Problem Formulation

Let $X=[x_1, x_2 \ldots x_n]^T \in \mathbb{R}^{n \times d}$ represent the input features obtained from n images of lung nodules each having a dimension d. Each data sample has an attribute/malignancy score given by $Y=[y_1, y_2 \ldots y_n]$, where $Y^T \in \mathbb{R}^{n \times 1}$. Generally, in CAD systems, X consists of features extracted from radiology images, and Y represents the malignancy score over 1-5 scale where 1 represents benign and 5 represents malignant. In supervised learning, the labeled training data is used to learn the coefficient vector or the regression estimator $W \in \mathbb{R}^d$. While testing, W is used to estimate Y for an unseen testing example.

For regression, a regularizer is often added to prevent over-fitting. Thus, a least square regression function with $\ell_1$ regularization can be represented as:

$$\min_W \|XW - Y\|_2^2 + \lambda \|W\|_1. \qquad (2)$$

In the above equation, the sparsity level of the coefficient vector $W=[w_1, w_2 \ldots w_d]$ is controlled by $\lambda$. It can be observed that Eq. 2 is an example of unconstrained convex optimization problem, which is not differentiable at $w_i=0$. So, for Eq. 2 the closed form solution with a global minimum is not feasible. In that case, the problem can be represented in the form of a constrained optimization function as:

$$\min_W \|XW - Y\|_2^2, \text{ s.t. } \|W\|_1 \leq t, \qquad (3)$$

where t and $\lambda$ observe inverse relationship. The function in Eq. 3 is convex and constraints define a convex set. As it is a convex problem, a local minimizer of the objective function is subjected to constraints corresponding to a global minimizer. This supervised setting is extended in deep learning and multi-task learning (MTL) to characterize nodules as benign or malignant.

3D Convolution Neural Network and Fine-Tuning

The inventors used a 3D CNN trained on a Sports-1M dataset and fine-tuned it on the lung nodule CT dataset. (Tran, D., Bourdev, L., Fergus, R., Torresani, L., Paluri, M.: Learning spatiotemporal features with 3D convolutional networks. In: ICCV. pp. 4489-4497. IEEE (2015); Karpathy, A., Toderici, G., Shetty, S., Leung, T., Sukthankar, R., Fei-Fei, L.: Large-scale video classification with convolutional neural networks. In: IEEE CVPR. pp. 1725-1732 (2014)). The Sports-1M dataset consists of 487 classes with 1 million videos. As the lung nodule dataset does not have a large number of training examples, fine-tuning is conducted to acquire dense feature representation from the Sports-1M. The 3D CNN architecture consists of 5 sets of convolution, 2 fully-connected and 1 soft-max classification layers. Each convolution set is followed by a max-pooling layer. The input to the 3D CNN comprises dimensions of 128×171×16, where 16 denotes the number of slices. Note that the images in the dataset are resized to have consistent dimensions such that the number of channels is 3 and the number of slices is fixed to 16. Hence, the overall input dimension can be considered as 3×16×128×171. The number of filters in the first 3 convolution layers are 64, 128 and 256 respectively, whereas there are 512 filters in the last 2 layers. The fully-connected layers have a dimension 4096 which is also the length of feature vectors used as an input to the Multi-task learning (MTL) framework.

Multi-Task Learning (MTL)

Figure 5A:
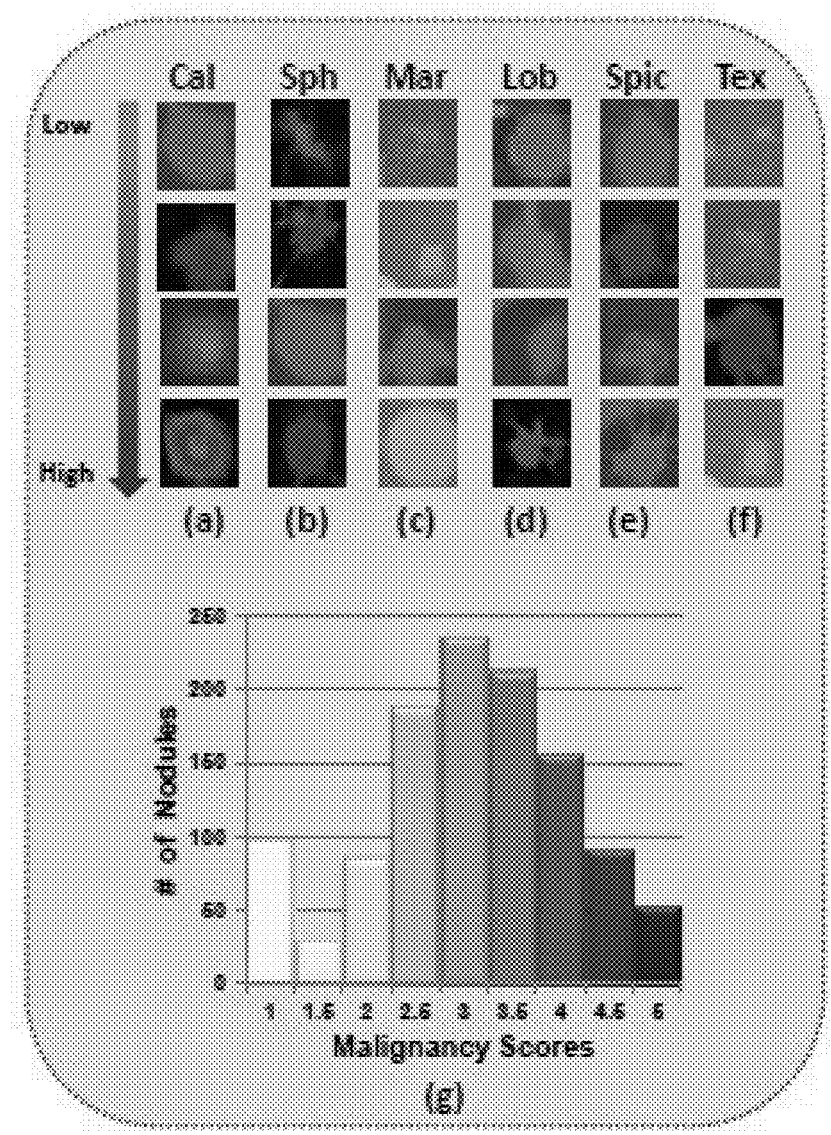
FIG. 5A is an image depicting lung nodule attributes and an overview of the proposed supervised approach. Visualization of lung nodules having different levels of attributes. On moving from the top (attribute absent) to the bottom (attribute prominently visible), the prominence level of the attribute increases. Different attributes including calcification, sphericity, margin, lobulation, speculation and texture can be seen in (a-f). The graph in (g) depicts the number of nodules with different malignancy levels in the experiments using the publicly available dataset.

Multi-task learning (MTL) is an approach of learning multiple tasks simultaneously while considering disparities and similarities across those tasks. Given M tasks, the goal is to improve the learning of a model for task i, where i∈M, by using the information contained in the M tasks. The inventors formulated the malignancy prediction of lung nodules as an MTL problem, where visual attributes of lung nodules are considered as distinct tasks (FIG. 5A). In a typical MTL problem, initially the correlation between M tasks and the shared feature representations are not known. The aim in the MTL approach is to learn a joint model while exploiting the dependencies among visual attributes (tasks) in feature space. In other words, visual attributes are utilized and exploit their feature level dependencies so as to improve regressing malignancy using other attributes.

Figure 5B:
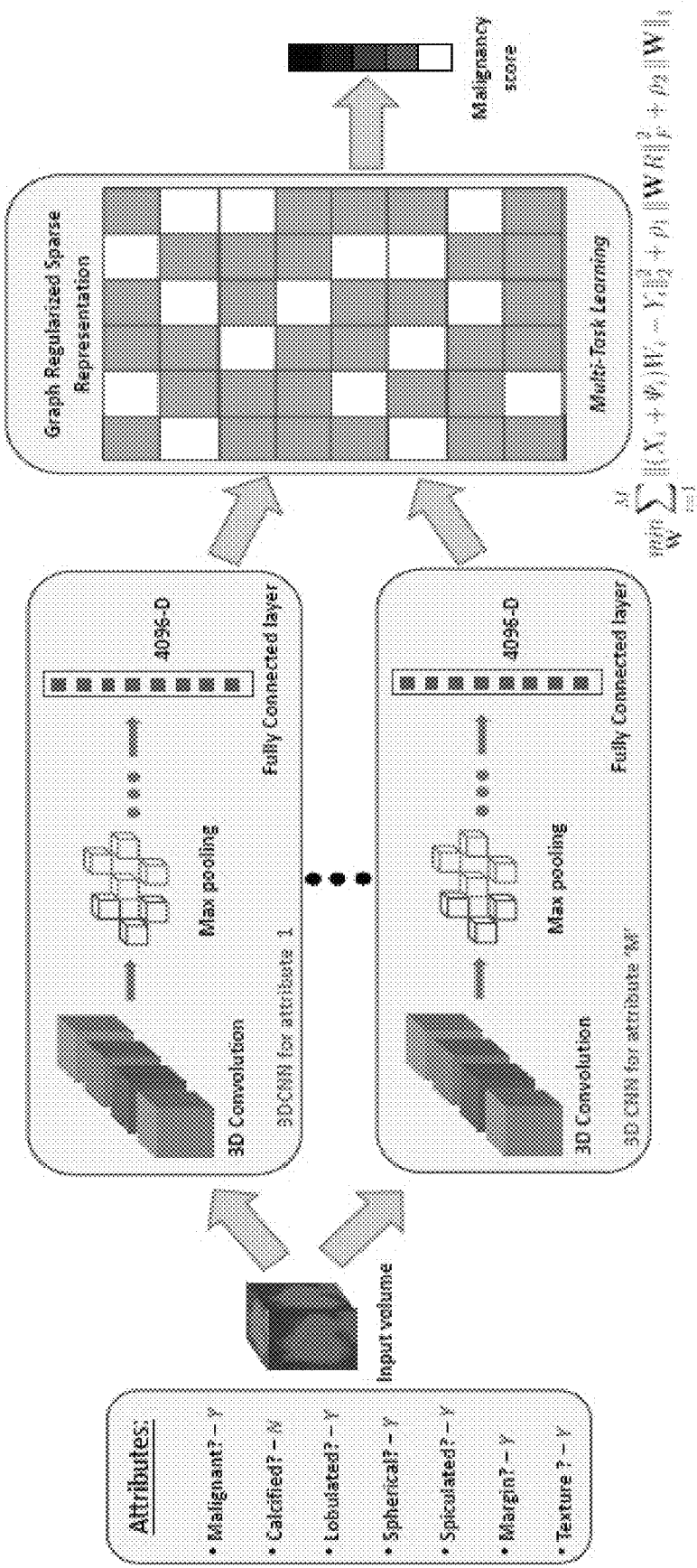
FIG. 5B is an image showing an overview of the proposed 3D CNN based graph regularized sparse MTL approach.

As shown in FIG. 5B, lung tumor characterization was designed as an MTL problem, where each task has model parameters $W_m$, which are utilized to characterize the corresponding task m. Moreover, when $W=[W_1, W_2 \ldots W_M] \in \mathbb{R}^{d \times M}$ constitutes a rectangular matrix, rank can be considered as a natural extension to cardinality, and nuclear/trace norm leads to low rank solutions. In some cases, nuclear norm regularization can be considered as the $\ell_1$-norm of the singular values. (Recht, B., Fazel, M., Parrilo, P. A.: Guaranteed minimum-rank solutions of linear matrix equations via nuclear norm minimization. SIAM review 52(3), 471-501 (2010)). Trace norm, the sum of singular values, is the convex envelope of the rank of a matrix (which is non-convex), where the matrices are considered on a unit ball. After substituting, $\ell_1$-norm by trace norm in Eq. 2, the least square loss function with trace norm regularization can be formulated as:

$$\min_W \sum_{i=1}^{M} \|X_i W_i - Y_i\|_2^2 + \rho \|W\|_*, \quad (4)$$

where p adjusts the rank of the matrix W, and $\|W\|_a = \sum_{i=1} \sigma_i(W)$ is the trace-norm where a denotes singular values. However, as in trace-norm, the assumption about models sharing a common subspace is restrictive for some applications.

As the task relationships are often unknown and are learned from data, tasks and their relations were represented in the form of a graph. Let T=(V,E) represent a complete graph in which nodes V correspond to the tasks and the edges E model any affinity between the tasks. In such case, a regularization can be applied on the graph modeling task dependencies. (Karpathy, A., Toderici, G., Shetty, S., Leung, T., Sukthankar, R., Fei-Fei, L.: Large-scale video classification with convolutional neural networks. In: IEEE CVPR.

pp. 1725-1732 (2014)). The complete graph can be modeled as a structure matrix $S=[e^1, e^2 \ldots e^{|E|}] \in \mathbb{R}^{M \times \|E\|}$ where the deviation between the pairs of tasks can be regularized as:

$$\|WS\|_F^2 = \sum_{i=1}^{\|E\|} \|We^i\|_2^2 = \sum_{i=1}^{\|E\|} \|W_{e_a^i} - W_{e_b^i}\|_2^2, \quad (5)$$

here, $e_{a2}{}^i$ are the edges between the nodes a and b, where $e^i \in \mathbb{R}^M$. The matrix S defines an incidence matrix where $e_a{}^i$ and $e_b{}^i$ are assigned to 1 and −1 respectively if nodes a and b are connected in the graph. Eq. 5 can be further explained as:

$$\|WS\|_F^2 = tr((WS)^T(WS)) = tr(WSS^TW^T) = tr(WLW^T) \quad (6)$$

where $\mathcal{L} = SS^T$ is the Laplacian matrix and 'tr' represents the trace of a matrix. The method to compute structure matrix S is discussed later in this example.

There may exist disagreements between the scores from different experts (radiologists) due to the inherent uncertainty in their evaluations. For instance, while one radiologist may give a malignancy score of $x_1^j$ to a nodule j, the other may give a score of $x_2^j$. In order to reflect these uncertainties in the algorithm, the inventors formulated a scoring function which models these inconsistencies:

$$\Psi(j) = \left(\exp\left(\frac{-\sum_r (x_r^j - \mu^j)^2}{2\sigma^j}\right)\right)^{-1}. \quad (7)$$

For a particular sample j, this inconsistency measure can be represented as is the score given by the $r^{th}$ radiologist (expert) whereas $\mu^j$ and $\sigma^j$ represent mean and standard deviation of the scores, respectively. For simplicity, the inventors have omitted the index for the task; however, this inconsistency score is calculated for all the tasks under consideration. The final objective function of graph regularized sparse least square optimization with the inconsistency measure can be expressed as:

$$\min_W \sum_{i=1}^{M} \underbrace{\|(X_i + \Psi_i)W_i - Y_i\|_2^2}_{①} + \underbrace{\rho_1 \|WS\|_F^2}_{②} + \underbrace{\rho_2 \|W\|_1}_{③}, \quad (8)$$

where $\rho^1$ tunes the penalty degree for graph structure and $\rho^2$ handles the sparsity level. In Eq. 8, the least square loss function ① observes decoupling of tasks whereas ② and ③ model their interdependencies, so as to learn joint representation.

Optimization

In order to solve Eq. 8, the conventional approach is to use standard gradient descent.

However, standard gradient descent cannot be applied here because the $l_1$-norm is not differentiable at W=0 and gradient descent approach fails to provide sparse solutions. (Recht, 2010). The optimization function in the above equation has both smooth and non-smooth convex parts. In this case, the function can be solved by estimating the non-smooth part. The $l_1$-norm in the above equation constitutes the non-smooth part and the proximal operator can be used for its estimation. Therefore, the inventors utilized accelerated proximal gradient method to solve Eq. 8. (Zhou, J., Chen, J., Ye, J.: MALSAR: Multi-task learning via structural regularization (2012)). The accelerated proximal approach is the first order gradient method having a convergence rate of $O(1/m^2)$, where m controls the number of iterations.

Materials (the same materials were used for Example 3 Unsupervised Learning below)

Data for Lung Nodules

For test and evaluation, the inventors used LIDC-IDRI dataset from Lung Image Database Consortium, which is one of the largest publicly available lung nodule dataset. (Armato III, S., McLennan, G., Bidaut, L., McNitt-Gray, M. F., Meyer, C. R., Reeves, A. P., Zhao, B., Aberle, D.R., Henschke, C. I., Hoffman, E. A., et al.: The Lung Image Database Consortium (LIDC) and Image Database Resource Initiative (IDRI): a completed reference database of lung nodules on CT scans. Medical Physics 38(2), 915-931 (2011)). The dataset comprises 1018 CT scans with a slice thickness varying from 0.45 mm to 5.0 mm. At most four radiologists annotated those lung nodules which have diameters equal to or greater than 3.0 mm.

The inventors considered nodules which were interpreted by at least three radiologists for evaluations. The number of nodules fulfilling this criterion was 1340. As a nodule may have different malignancy and attribute scores provided by different radiologists, their mean scores were used. The nodules have scores corresponding to these six attributes: (i) calcification, (ii) lobulation, (iii) spiculation, (iv) sphericity, (v) margin and (vi) texture as well as malignancy (FIG. 5). The malignancy scores ranged from 1 to 5 where 1 denoted benign and 5 meant highly malignant nodules. To account for malignancy indecision among radiologists, the inventors excluded nodules with a mean score of 3. The final evaluation set included 509 malignant and 635 benign nodules. As a preprocessing step, the images were resampled to be isotropic so as to have 0.5 mm spacing in each dimension.

Data for IPMN

Figure 6:
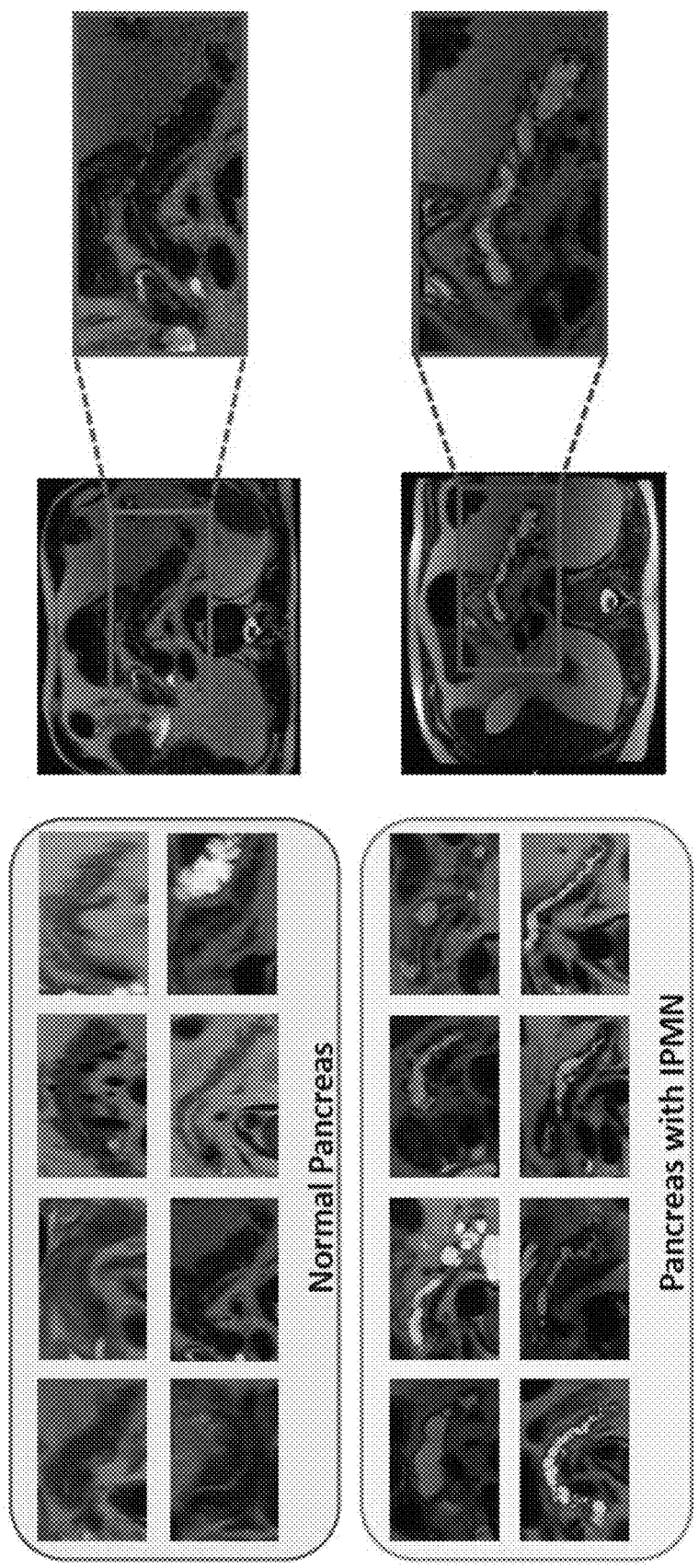
FIG. 6 is a series of images depicting axial T2 MRI scans illustrating the pancreas. The top row shows different ROIs of the pancreas, along with a magnified view of a normal pancreas (outlined in blue). The bottom row shows ROIs from subjects with IPMN in the pancreas (outlined with red).

The data for the classification of IPMN contains T2 Mill axial scans from 171 subjects. The scans were labeled by a radiologist as normal or IPMN. Out of 171 scans, 38 subjects were normal, whereas the rest of 133 were from subjects diagnosed with IPMN. The in-plane spacing (xy-plane) of the scan was ranging from 0.468 mm to 1.406 mm. As preprocessing, the inventors first employ N4 bias field correction to each image in order to normalize variations in image intensity. (Tustison, N. J., Avants, B. B., Cook, P. A., Zheng, Y., Egan, A., Yushke-vich, P. A., Gee, J. C.: N4ITK: Improved N3 bias correction. IEEE Transactions on Medical Imaging 29(6), 1310-1320 (2010)). The inventors then applied a curvature anisotropic image filter to smooth each image while preserving edges. For experiments, 2D axial slices with pancreas (and IPMN) are cropped to generate Region of Interest (ROI) as shown in FIG. 6. The large intra-class variation, especially due to varying shapes of the pancreas can also be observed in FIG. 6. A list of different supervised and unsupervised learning experiments along with their evaluation sets is tabulated in Table 2 below.

TABLE 2

Different Experiments Performed for Supervised and Unsupervised Learning Along with their Evaluation Sets

| Experiments | Details | Evaluation Set |
|---|---|---|
| E1 | Supervised learning, 3D CNN based Multi-task learning with attributes, fine-tuning (C3D) network | 3D dataset: Malignancy score regression of Lung nodules (CT) |
| E2 | Unsupervised learning, GIST features, Proportion-SVM | 2D dataset: Lung nodules (CT) and IPMN classification (MRI) |
| E3 | Unsupervised learning, features from different layers of 2D VGG network | |
| E4 | Supervised learning to establish classification upper-bound, GIST and VGG features with SVM and RF | |

Results

The inventors fine-tuned the 3D CNN network trained on Sports-1M dataset which had 487 classes. (Amato, 2011). In order to train the network with binary labels for malignancy and the six attributes the inventors used the mid-point as pivot and labeled samples as positive (or negative) based on their scores being greater (or lesser) than the mid-point. In the context, malignancy and attributes are characterized as tasks. The C3D was fine-tuned with these 7 tasks and 10-fold cross-validation was conducted. The requirement to have a large amount of labeled training data was evaded by fine-tuning the network. Since the input to the network required 3 channel image sequences with at least 16 slices, the inventors concatenated the gray level axial channel as the other two channels.

Additionally, in order to ascertain that all input volumes have 16 slices, interpolation was performed where warranted. The final feature representation was obtained from the first fully connected layer of 3D CNN consisting of 4096-dimensions.

For computing structure matrix S, the correlation between different tasks was calculated by estimating the normalized coefficient matrix W via least square loss function with lasso followed by the calculation of correlation coefficient matrix. (Karpathy, 2014). In order to get a binary graph structure matrix, the correlation coefficient matrix was thresholded. As priors in Eq. (8) the inventors used and as 1 and 10 respectively. Finally, to obtain the malignancy score for test images, the features from the network trained on malignancy were multiplied with the corresponding task coefficient vector W.

The inventors evaluated the proposed approach using both classification and regression metrics. For classification, a nodule was considered to be successfully classified if its predicted score lies in +1 of the ground truth score. For regression, average absolute score difference was calculated between the predicted score and the true score. The comparison of the proposed MTL approach with approaches including GIST features, 3D CNN features from pre-trained network+LASSO, Ridge Regression (RR) and 3D CNN MTL+trace norm is tabulated in Table 3. It was observed that the proposed graph regularized MTL performs significantly better than other approaches both in terms of classification accuracy as well as the mean score difference. The gain in classification accuracy was found to be 15% and 11% for GIST and Trace norm respectively. In comparison with the pre-trained network, an improvement of 5% was obtained with proposed MTL. In addition, the proposed approach reduces the average absolute score difference for GIST by 32% and for Trace norm by 27%.

TABLE 3

Comparison of the Claimed Approach with Other Methods Using
Regression Accuracy and Mean Absolute Score Difference for
Lung Nodule Characterization

| Methods | Accuracy % | Mean Score Difference |
|---|---|---|
| GIST features + LASSO | 76.83 | 0.675 |
| GIST features + RR | 76.48 | 0.674 |
| 3D CNN features + LASSO (Pre-trained) | 86.02 | 0.530 |
| 3D CNN features + RR (Pre-trained) | 82.00 | 0.597 |
| 3D CNN features + LASSO (Fine-tuned) | 88.04 | 0.497 |
| 3D CNN features + RR (Fine-tuned) | 84.53 | 0.550 |
| 3D CNN MTL with Trace norm | 80.08 | 0.626 |
| Proposed (3D CNN with Multi-task Learning-Eq. 8) | 91.26 | 0.459 |

In order to establish the upper-bound on the classification performance, the inventors trained linear SVM and Random Forest using GIST and different deep learning features with ground truth labels on the same 10-fold cross-validations sets. Table 4 lists the classification accuracy, sensitivity, and specificity using GIST, VGG-fc7 and VGG-fc8 features for both IPMN and lung nodules. For both VGG-fc7 and VGG-fc8, the inventors used features after ReLU since they are found to be more discriminative (FIG. 8). Interestingly, for lung nodules, VGG-fc7 features along with RF classifier are reported to have comparable results to the combination of GIST and RF classifier. This can be explained by the fact that deep networks are pre-trained on ImageNet dataset as compared to handcrafted features such as GIST, which do not require any training. On the other hand, for smaller datasets such as IPMN, deep features are found to perform better as compared to GIST. In order to balance the number of positive (IPMN) and negative (normal) examples, which can be a critical drawback otherwise, the inventors performed Adaptive Synthetic Sampling. (Oliva, A., Torralba, A.: Modeling the shape of the scene: A holistic representation of the spatial envelope. IJCV 42(3), 145-175 (2001)). This was done to generate synthetic examples in terms of features from the minority class (normal).

TABLE 4

Classification of IPMN and Lung Nodules Using
Different Features and Supervised Learning Classifiers

| Evaluation Set | Features | Classifiers | Accuracy (%) | Sensitivity (%) | Specificity (%) |
|---|---|---|---|---|---|
| IPMN Classification | GIST | SVM | 76.05 | 83.65 | 52.67 |
| | | RF | 81.9 | 93.69 | 43.0 |
| | VGG-fc7 | SWM | 84.18 | 96.91 | 44.83 |
| | | RF | 81.96 | 94.61 | 42.83 |
| | VGG-fc8 | SVM | 84.22 | 97.2 | 46.5 |
| | | RF | 80.82 | 93.4 | 45.67 |
| Lung Nodule Classification | GIST | SVM | 81.56 | 71.31 | 90.02 |
| | | RF | 81.64 | 76.47 | 85.97 |
| | VGG-fc7 | SVM | 77.97 | 75.2 | 80.6 |
| | | RF | 81.73 | 78.24 | 84.59 |
| | VGG-fc8 | SVM | 78.76 | 74.67 | 82.29 |
| | | RF | 80.51 | 76.03 | 84.24 |

Conclusion

The inventors analyzed the significance of different imaging attributes corresponding to lung nodules including speculation, texture, calcification and others for risk assessment. Instead of manually modeling these attributes, the inventors utilized 3D CNN to learn rich feature representations associated with these attributes. The graph regularized sparse MTL framework was employed to integrate 3D CNN features from these attributes. The inventors found that the features associated with these attributes were complementary to those corresponding to malignancy.

Example 3

Tumor Characterization Using Unsupervised Learning

Since annotating medical images is laborious, expensive and time-consuming, the inventors also developed an unsupervised learning method to classify lung nodules and IPMN by using a novel algorithm to address the limited availability of labeled training data, a common problem in medical imaging applications. Inspired by learning from label proportion (LLP) approaches in computer vision, the inventors used proportion-SVM for characterizing tumors. First, the inventors extracted discriminative information from a large amount of unlabeled imaging data. The inventors analyzed both hand-crafted and deep learning features and assessed how good those features were when applied to tumor characterization. In order to obtain an initial set of labels in an unsupervised fashion, the samples are clustered into different groups in the feature domain. The inventors then trained Proportion-Support Vector Machine (aSVM) algorithm using label proportions rather than instance labels. The trained model is then employed to learn malignant-benign categorization of the tumors.

Figure 7:
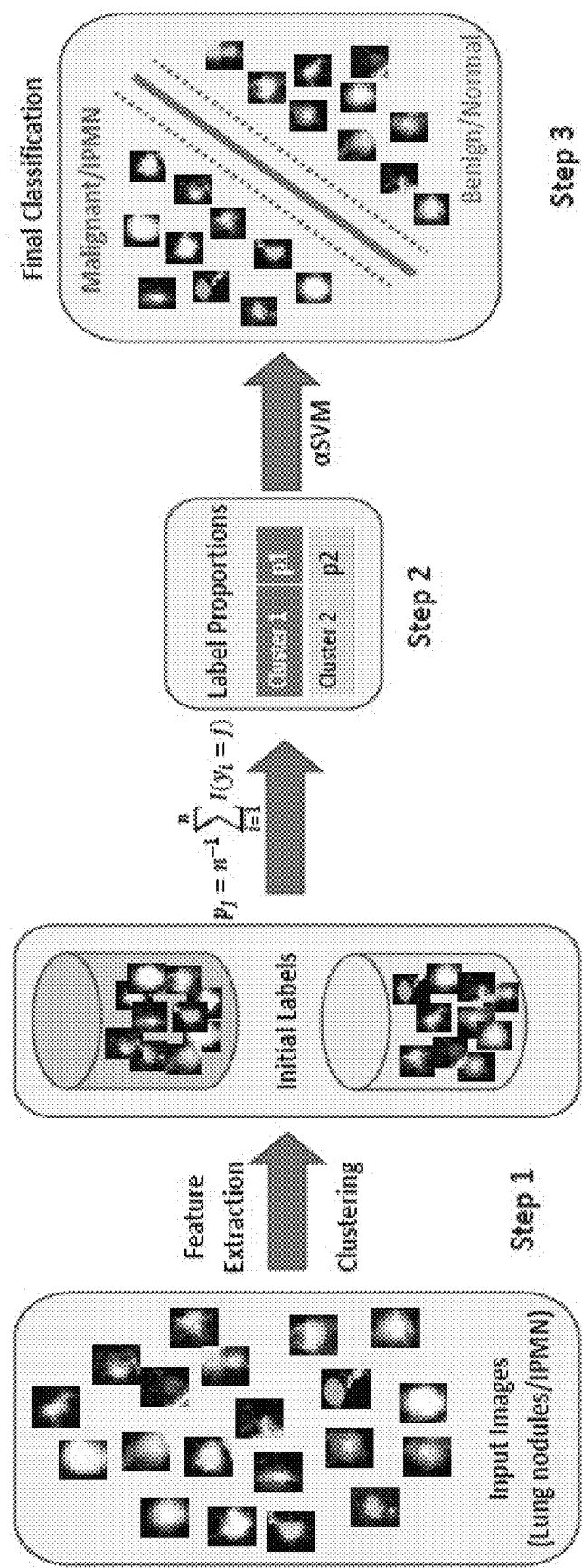
FIG. 7 is an image depicting an outline of the proposed unsupervised approach. Given the input images, the GIST features are computed and k-means clustering is performed to get the initial set of labels which can be noisy. Using the set of labels, label proportions are computed corresponding to each cluster/group (Eq. 10). Finally, aSVM is employed to learn a discriminative model using the features and label proportions.

As illustrated in FIG. 7, the proposed unsupervised framework includes three steps.

First, the inventors perform clustering on the appearance features obtained from the images to estimate an initial set of labels. Using the obtained initial labels, the inventors computed label proportions corresponding to each cluster. A classifier is then trained using the label proportions and clusters to obtain a final classification.

Initial Label Estimation

Let $X=[x_1, x_2 \ldots x_n]^T \in \mathbb{R}^{n \times d}$ represent the input matrix which contains features from n images such that $x \in \mathbb{R}^d$. In order to obtain an initial set of labels corresponding to each sample, the inventors clustered the data into $2 \leq k < n$ clusters using k means. Let A represent $|X| \times k$ assignment matrix which denotes the membership assignment of each sample to a cluster. The optimal clustering would minimize the following objective function:

$$\underset{\mu_v, A}{\text{argmin}} \sum_{v=1}^{k} A(u, v)\|x_u - \mu_v\|^2, \quad (9)$$

$$s.t. \quad A(u, v) = 0 \vee 1, \sum_j A(u, v) = 1$$

where $\mu_v$ is the mean of the samples in cluster v. The label $c_u$ for the $u^{th}$ sample can then be estimated as:

$$c_u = \underset{v}{\text{argmax}} A(u, v) \quad (10)$$

These labels serve as an initial set used to estimate label proportions which are then used to train proportion-SVM ($\alpha$SVM) for further improvements. It is important to note that when data is divided into groups/clusters through clustering, one may assume that each cluster corresponds to a particular class. Here, clustering is used to estimate an initial set of labels that is progressively refined in the subsequent steps.

Learning with the Estimated Labels

Since the initial label estimation approach is unsupervised, there are uncertainties associated with them. It is, therefore, reasonable to assume that learning a discriminative model based on these noisy instance level labels can deteriorate classification performance. In order to address this issue, the inventors modeled the instance level labels as latent variables and thereby consider group/bag level labels.

Inspired by $\alpha$SVM approach, which models the latent instance level variables using the known group level label proportions, the inventors formulated the learning problem such that clusters are analogous to the groups. (Shalev-Shwartz, S., Tewari, A.: Stochastic methods for l1-regularized loss minimization. Journal of Machine Learning Research 12(June), 1865-1892 (2011)). In the formulation, each cluster j can be represented as a group such that the majority of samples belong to the class j. Considering the groups to be disjoint such that, and represents groups; the objective function of the large-margin $\alpha$SVM after convex relaxation can be formulated as:

$$\min_{c \in C} \min_{w} \left( \frac{1}{2} w^T w + K \sum_{u=1}^{n} L(c_u, w^T \phi(x)) \right) \quad (11)$$

$$C = \{c | |\tilde{p}_u(c) - p_v| \le \epsilon, c_u \in \{-1, 1\} \forall_{v=1}^{k}\},$$

where $\tilde{p}$ and p represent the estimated and true label proportions, respectively. In Eq. 11, c is the set of instance level labels, $\phi(.)$ is the input feature, K denotes cost parameter and L(.) represents the hinge-loss function for maximum-margin classifiers such as SVM. An alternative approach based on training a standard SVM classifier with clustering assignments is discussed later in this example.

The optimization in Eq. 11 is an instance of Multiple Kernel Learning, which can be solved using the cutting plane method where the set of active constraints is incrementally computed. The goal is to find the most violated constraint, however, the objective function still decreases even by further relaxation and aiming for any violated constraint.

Calculated Label Proportions

In the conventional $\alpha$SVM approach, the label proportions are known a priori. Since the approach is unsupervised, both instance level labels and group label proportions are unknown. Moreover, establishing strong assumptions about the label proportions may affect learning. It is, however, reasonable to assume that a large number of instances in any group carry the same label and there may be a small number of instances which are outliers. The label proportions serve as a soft-label for a bag where a bag can be considered as a super-instance. In order to determine the label proportions in a data-driven manner, the inventors use the estimated labels obtained from clustering. The label proportion $p_j$ corresponding to the group j can be represented as:

$$p_j = n^{-1} \sum_{i=1}^{n} I(y_i = j), \quad (12)$$

Where I(.) is the indicator function which yields 1 when $y_i = j$. The $\alpha$SVM is trained using the image features and label proportions to classify the testing data. It is important to mention that the ground truth labels (benign/malignant labels) are used only to evaluate the proposed framework and are not used in estimating label proportions or training of the proportion-SVM. In addition, clustering and label proportion calculations are only performed on the training data and the testing data remains completely unseen for $\alpha$SVM. The number of clusters is fixed at 2, i.e. benign and malignant classes and the results was checked to assign benign and malignant labels to the clusters.

Materials (the same materials were used for Example 2 Supervised Learning above)

Data for Lung Nodules

For test and evaluation, the inventors used LIDC-IDRI dataset from Lung Image Database Consortium, which is one of the largest publicly available lung nodule dataset. (Amato, 2011). The dataset comprises 1018 CT scans with a slice thickness varying from 0.45 mm to 5.0 mm. At most four radiologists annotated those lung nodules which have diameters equal to or greater than 3.0 mm.

The inventors considered nodules which were interpreted by at least three radiologists for evaluations. The number of nodules fulfilling this criterion was 1340. As a nodule may have different malignancy and attribute scores provided by different radiologists, their mean scores were used. The nodules have scores corresponding to these six attributes: (i) calcification, (ii) lobulation, (iii) spiculation, (iv) sphericity, (v) margin and (vi) texture as well as malignancy (FIG. 5). The malignancy scores ranged from 1 to 5 where 1 denoted benign and 5 meant highly malignant nodules. To account for malignancy indecision among radiologists, the inventors excluded nodules with a mean score of 3. The final evaluation set included 509 malignant and 635 benign nodules. As a preprocessing step, the images were resampled to be isotropic so as to have 0.5 mm spacing in each dimension.

Data for IPMN

The data for the classification of IPMN contains T2 MRI axial scans from 171 subjects. The scans were labeled by a radiologist as normal or IPMN. Out of 171 scans, 38 subjects were normal, whereas the rest of 133 were from subjects diagnosed with IPMN. The in-plane spacing (xy-plane) of the scan was ranging from 0.468 mm to 1.406 mm. As preprocessing, the inventors first employ N4 bias field correction to each image in order to normalize variations in image intensity. (Tustison, 2010). The inventors then apply curvature anisotropic image filter to smooth image while preserving edges. For experiments, 2D axial slices with pancreas (and IPMN) are cropped to generate Region of Interest (ROI) as shown in FIG. 6. The large intra-class variation, especially due to varying shapes of the pancreas can also be observed in FIG. 6. A list of different supervised and unsupervised learning experiments along with their evaluation sets is tabulated in Table 2.

Results

For unsupervised learning, evaluations were performed on both lung nodules and IPMN datasets. In order to compute image level features, the inventors used GIST descriptors. (Yu, 2013). The number of clusters is fixed as 2, which accounts for benign and malignant classes. The clustering result was checked to assign benign and malignant labels to the clusters. The inventors used 10-fold cross-validation to evaluate the proposed approach. The training samples along with the label proportions generated using clustering served as the input to αSVM with a linear kernel.

To evaluate the unsupervised approach the inventors used accuracy, sensitivity and specificity as metrics. It was observed in Table 5 that the proposed combination of clustering and αSVM significantly outperforms other approaches in accuracy and sensitivity. In comparison with clustering+SVM, the proposed framework yields almost 21% improvement in sensitivity for lung nodules and around 7% improvement for IPMN classification. The low sensitivity and high specificity of clustering, clustering+SVM, and clustering+RF approaches can be explained by disproportionate assignment of instances as benign (normal) by these approaches, which is not found in the proposed approach. At the same time, the proposed approach records around 24% and 9% improvement in accuracy as compared to clustering for lung nodules and IPMN, respectively.

TABLE 5

Average Classification Accuracy, Sensitivity and Specificity of the Proposed Unsupervised Approach for IPMN and Lung Nodule Classification with Other Methods

| Evaluation Set | Methods | Accuracy | Sensitivity | Specificity |
| --- | --- | --- | --- | --- |
| IPMN Classification | Clustering | 49.18% | 45.34% | 62.83% |
| | Clustering + RF | 53.20% | 51.28% | 69.33% |
| | Clustering + SVM | 52.03% | 51.96% | 50.5% |
| | Proposed approach | 58.04% | 58.61% | 41.67% |
| Lung Nodule Classification | Clustering | 54.83% | 48.69% | 60.04% |
| | Clustering + RF | 76.74% | 58.59% | 91.40% |
| | Clustering + SVM | 76.04% | 57.08% | 91.28% |
| | Proposed approach | 78.06% | 77.85% | 78.28% |

Given the success of deep learning features for image classification tasks and their popularity with the medical imaging community, the inventors explored their performance to classify lung nodules and IPMN in an unsupervised manner. For this purpose, the inventors used a pretrained deep CNN architecture to extract features and then perform clustering to obtain baseline classification performance. Features were extracted from fully connected layers 7 and 8 of Fast-VGG with and without applying ReLU non-linearity. (Tustison, 2010). Classification accuracy, using clustering over these features is shown in FIG. 8.

As shown in FIG. 8, the features with nonlinearity (ReLU) are more discriminative for classification using clustering as compared to without ReLU. The same trend can be observed for both lung nodules and IPMN classification using VGG-fc7 and VGG-fc8 layers. Owing to the larger evaluation set, the influence of ReLU is more prominent for lung nodules as compared to IPMN. Although the results between VGG-fc7 and VGG-fc8 are not substantially different, highest accuracy for IPMN can be obtained by using VGGfc7-ReLU features and for lung nodules by using VGG-fc8—ReLU features. The non-linearity induced by ReLU clips the negative values to zero, which can sparsify the feature vector and can reduce overfitting. Additionally, it can be seen that GIST features yield comparable performance than deep features (Table 5). This can be explained by the fact that the deep networks were trained on ImageNet dataset so the filters in the networks were more tuned to the variations in natural images than medical images. Classification improvement can be expected with unsupervised feature learning techniques such as GANs. (Kallenberg, M., Petersen, K., Nielsen, M., Ng, A. Y., Diao, P., Igel, C., Vachon, C. M., Holland, K., Winkel, R. R., Karssemeijer, N., et al.: Unsupervised deep learning applied to breast density segmentation and mammographic risk scoring. IEEE transactions on medical imaging 35(5), 1322-1331 (2016)).

The future prospects of using different architectures to perform unsupervised representation learning using GAN are promising. Instead of using hand-engineered priors of sampling in the generator, the work in He et al. learned priors using denoising auto-encoders. (He, H., Bai, Y., Garcia, E.A., Li, S.: ADASYN: Adaptive synthetic sampling approach for imbalanced learning. In: Neural Networks, 2008. IJCNN 2008. (IEEE World Congress on Computational Intelligence). IEEE International Joint Conference on. pp. 1322-1328. IEEE (2008)). For measuring the sample similarity for complex distributions such as those in the images, Kalb et al. jointly trained variational autoencoders and GANs. (Kalb, B., Sarmiento, J. M., Kooby, D. A., Adsay, N. V., Martin, D. R.: MR imaging of cystic lesions of the pancreas. Radiographics 29(6), 1749-1765 (2009 Kalb, B., Sarmiento, J. M., Kooby, D. A., Adsay, N. V., Martin, D. R.: MR imaging of cystic lesions of the pancreas. Radiographics 29(6), 1749-1765 (2009)). Moreover, the applications of CatGAN and InfoGAN for semi-supervised and unsupervised classification tasks in medical imaging are worth exploring as well. (Ma, L., Lu, Z., Shang, L., Li, H.: Multimodal convolutional neural networks for matching image and sentence. In: IEEE ICCV. pp. 2623-2631 (2015); Nguyen, A., Yosinski, J., Bengio, Y., Dosovitskiy, A., Clune, J.: Plug & play generative networks: Conditional iterative generation of images in latent space. arXiv preprint arXiv: 1612.00005 (2016)).

There is a lot of potential for research in developing unsupervised approaches for medical imaging applications. Medical imaging has unique challenges associated with the scarcity of labeled examples. Moreover, unless corroborated by biopsy, there may exist a large variability in labeling from different radiologists. Although fine-tuning has helped to address the lack of annotated examples, the performance is limited due to large differences in domains. It is comparatively easier to obtain scan level labels than slice level labels. In this regard, weakly supervised approaches such as multiple instance learning (MIL) can be of great value. Active learning can be another solution to alleviate the difficulty in labeling. Deep learning for joint feature learning and clustering can be employed to obtain data-driven clusters. (Larsen, A.B.L., Snderby, S. K., Larochelle, H., Winther, O.: Autoencoding beyond pixels using a learned similarity metric. In: ICML (2016)). In future, these research directions can be pursued to address unique medical imaging challenges and to have improved diagnostic decisions in clinics.

Conclusion

The inventors have developed a method of automatically detecting and diagnosing neoplasms from imaging scans using a combination of 3D CNN architecture with supervised or unsupervised deep learning methods. For diagnosis, the inventors have developed a new deep learning method for nodule detection from imaging scans designed as a single 3D CNN with dense connections, trained in an end-to-end manner. The method uses a single feed forward pass of a single network for detection and provides better performance as compared to currently available techniques. The inventors have also developed both supervised learning and unsupervised learning methods to classify malignancy of the detected nodule. In the supervised learning method, the inventors use a 3D CNN with transfer learning and incorporation of task dependent feature representations into a CAD system via a graph-regularized sparse Multi-Task Learning (MTL) framework. For the unsupervised learning system, the inventors have addressed the limited availability of labeled training data by developing a method in which clustering is performed on imaging attributes of the nodule to estimate labels used for label proportions which are then used with a new classifier algorithm, proportion-SVM ($\alpha$-SVM) to characterize the tumor types. Both the detection and the diagnosis aspects of the method were shown to perform better than those techniques currently used in the art. The combination of the detection and diagnosis methods allows for automatic detection and diagnosis of neoplasms/nodules and eliminates the need for numerous samples and large variability in labeling from different radiologists.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

While there has been described and illustrated specific embodiments of the invention, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall there between.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of detecting and diagnosing cancer characterized by presence of at least one nodule in a subject comprising:
    providing an imaging scan of the subject;
    automatically detecting the presence of the at least one nodule in the imaging scan using a volumetric method of the whole imaging scan, the volumetric method using a 3D convolutional neural network (CNN) having convolution blocks with dense connections wherein a cell-wise classification of input is done in a single feed forward path of the CNN in one shot to detect all of the at least one nodule in a given volume simultaneously and in the absence of postprocessing or other steps to remove false positives; and
    automatically determining a classification of malignancy of the at least one detected nodule in the imaging scan using a supervised or an unsupervised deep learning method;
    wherein the supervised learning method comprising
        automatically determining imaging attributes of the at least one nodule using transfer learning of a pre-trained 3D convolutional neural network (C3D);
        fine-tuning the C3D network with binary labels for malignancy and the imaging attributes; and
        incorporating the binary labels for malignancy and the binary labels for the imaging attributes of the at least one nodule into a graph regularized sparse multi-task learning (MTL) framework to obtain the classification of malignancy of the at least one nodule;
    wherein the unsupervised learning method comprising
        performing clustering on the imaging attributes of the at least one nodule to estimate an initial set of labels;
        computing label proportions corresponding to each cluster; and
        training a classifier using the label proportions and clusters to obtain the classification of malignancy of the at least one nodule.

2. The method of claim 1, wherein the input to the 3D CNN of the detection step is a 512×512×8 volume.

3. The method of claim 2, wherein output of the 3D CNN of the detection step is a 16×16×8 probability map representing likelihood of nodule presence.

4. The method of claim 1, wherein the 3D CNN of the detection step comprising:
    a total of 36 3D convolution layers wherein 6 convolution layers form each of 5 dense blocks and remaining convolution layers form transition layers;
    4 max-pooling layers;
    4 transition layers; and
    a sigmoid activation function.

5. The method of claim 1, wherein the cancer is lung cancer or pancreatic cancer.

6. The method of claim 1, wherein the imaging scan is created using computed tomography (CT), magnetic resonance imaging (MRI), positron emission tomography (PET), positron emission tomography/computed tomography (PET/CT), positron emission tomography/magnetic resonance imaging (PET/MRI) or contrast-enhanced ultrasound (CEUS).

7. The method of claim 1, wherein the imaging attributes are selected from the group consisting of calcification, speculation, sphericity, lobulation, margin, texture and combinations thereof.

8. The method of claim 1, wherein the classifier of the unsupervised learning method of the diagnosing step is proportion-support vector machine (aSVM).

9. A method of detecting and diagnosing lung cancer in a subject comprising:
provproviding a computed tomography (CT) scan of the subject; and
automatically detecting presence of at least one nodule in the CT scan using a volumetric method of the whole imaging scan, the volumetric method using a 3D convolutional neural network (CNN) having convolution blocks with dense connections wherein a cell-wise classification of input is done in a single feed forward path of the CNN in one shot to detect all of the at least one nodule in a given volume simultaneously and in the absence of postprocessing or other steps to remove false positives.

10. The method of claim 9, wherein the 3D CNN comprising:
a total of 36 3D convolution layers wherein 6 convolution layers form each of 5 dense blocks and remaining convolution layers form transition layers;
4 max-pooling layers;
4 transition layers; and
a sigmoid activation function.

11. The method of claim 9, further comprising:
automatically determining a classification of malignancy of the at least one detected nodule in the imaging scan using a supervised deep learning method wherein the supervised deep learning method comprising
automatically determining imaging attributes of the at least one nodule using transfer learning of a pre-trained 3D convolutional neural network (C3D);
fine-tuning the C3D network with binary labels for malignancy and the imaging attributes; and
incorporating the binary label for malignancy and the binary labels for the imaging attributes of the at least one nodule into a graph regularized sparse multi-task learning (MTL) framework to obtain the classification of malignancy of the at least one nodule.

12. The method of claim 11, wherein the imaging attributes are selected from the group consisting of calcification, speculation, sphericity, lobulation, margin, texture and combinations thereof.

13. The method of claim 9, further comprising:
automatically determining a classification of malignancy of the at least one detected nodule in the imaging scan using an unsupervised deep learning method wherein the unsupervised deep learning method comprising
performing clustering on the imaging attributes of the at least one nodule to estimate an initial set of labels;
computing label proportions corresponding to each cluster; and
training a classifier using the label proportions and clusters to obtain the classification of malignancy of the at least one nodule.

14. The method of claim 13, wherein the imaging attributes are selected from the group consisting of calcification, speculation, sphericity, lobulation, margin, texture and combinations thereof.

15. The method of claim 13, wherein the classifier of the unsupervised learning method is proportion-support vector machine ($\alpha$SVM).

16. A method of detecting and diagnosing pancreatic cancer in a subject comprising:
providing an imaging scan of the subject;
automatically detecting presence of the at least one neoplasm in the imaging scan using a volumetric method of the whole imaging scan, the volumetric method using a 3D convolutional neural network (CNN) having convolution blocks with dense connections wherein a cell-wise classification of input is done in a single feed forward path of the CNN in one shot to detect all of the at least one neoplasm in a given volume simultaneously and in the absence of postprocessing or other steps to remove false positives; and
automatically determining a classification of malignancy of the at least one detected neoplasm in the imaging scan using a supervised or an unsupervised deep learning method;
wherein the supervised deep learning method comprising
automatically determining imaging attributes of the at least one neoplasm using transfer learning of a pre-trained 3D convolutional neural network (C3D);
fine-tuning the C3D network with binary labels for malignancy and the imaging attributes; and
incorporating the binary label for malignancy and the binary labels for the imaging attributes of the at least one nodule into a graph regularized sparse multi-task learning (MTL) framework to obtain the classification of malignancy of the at least one neoplasm;
wherein the unsupervised deep learning method comprising
performing clustering on the imaging attributes of the at least one neoplasm to estimate an initial set of labels;
computing label proportions corresponding to each cluster; and
training a classifier using the label proportions and clusters to obtain the classification of malignancy of the at least one neoplasm.

17. The method of claim 16, wherein the 3D CNN of the diagnosing step comprising:
a total of 36 3D convolution layers wherein 6 convolution layers form each of 5 dense blocks and remaining convolution layers form transition layers;
4 max-pooling layers;
4 transition layers; and
a sigmoid activation function.

18. The method of claim 16, wherein the imaging scan is a magnetic resonance image (MRI) scan.

19. The method of claim 16, wherein the imaging attributes are selected from the group consisting of calcification, speculation, sphericity, lobulation, margin, texture and combinations thereof.

20. The method of claim 16, wherein the classifier of the unsupervised learning method is proportion-support vector machine ($\alpha$SVM).

* * * * *